(12) United States Patent  
Omasa

(10) Patent No.: US 8,062,501 B2
(45) Date of Patent: Nov. 22, 2011

(54) NEUTRAL ELECTROLYTIC WATER, NEUTRAL ELECTROLYTIC WATER PRODUCTION METHOD AND DEVICE THEREOF

(75) Inventor: Ryushin Omasa, Fujisawa (JP)

(73) Assignee: Ube Industries, Ltd., Yamaguchi (JP)

( * ) Notice: Subject to any disclaimer, the term of this patent is extended or adjusted under 35 U.S.C. 154(b) by 1262 days.

(21) Appl. No.: 11/660,118

(22) PCT Filed: Oct. 6, 2005

(86) PCT No.: PCT/JP2005/018528
§ 371 (c)(1),
(2), (4) Date: Feb. 12, 2007

(87) PCT Pub. No.: WO2006/041001
PCT Pub. Date: Apr. 20, 2006

(65) Prior Publication Data
US 2007/0215489 A1 Sep. 20, 2007

(30) Foreign Application Priority Data
Oct. 8, 2004 (JP) .................... 2004-296332

(51) Int. Cl.
*C02F 1/46* (2006.01)
(52) U.S. Cl. ........................ 205/742; 205/744

(58) Field of Classification Search .............. 205/742, 205/744
See application file for complete search history.

(56) References Cited

U.S. PATENT DOCUMENTS

| | | | | |
|---|---|---|---|---|
| 5,730,856 A | * | 3/1998 | Omasa | 205/742 |
| 6,627,053 B2 | * | 9/2003 | Hirota et al. | 204/228.1 |
| 6,632,347 B1 | * | 10/2003 | Buckley et al. | 205/620 |

FOREIGN PATENT DOCUMENTS

| | | |
|---|---|---|
| JP | 08-281272 | 10/1996 |
| JP | 09-040482 | 2/1997 |
| JP | 2002-102323 | 4/2002 |
| JP | 2004-122109 | 4/2004 |
| WO | WO 01/90003 A | 11/2001 |

* cited by examiner

*Primary Examiner* — Arun S Phasge
(74) *Attorney, Agent, or Firm* — Frommer Lawrence & Haug, LLP; Ronald R Santucci

(57) ABSTRACT

A device and method are provided for producing neutral electrolytic water usable in a wide range of fields and stable over long periods of time. In this invention, neutral electrolytic water is produced by an electrolysis process that applies a voltage of 1 volt to 30 volts, and current density of 5 A/dm$^2$ to 300 A/dm$^2$, from a direct current or pulsed current, to a liquid for processing comprised of water and at least one type of salt selected from a group consisting of NaCl, KCl, and CaCl$_2$ while vibrating that liquid at an amplitude from 0.01 to 15 millimeters at a period between 10 Hertz and 200 Hertz.

6 Claims, 22 Drawing Sheets

FIG.5

| PART NO. | PART NAME |
|---|---|
| 1 | FRAME |
| 2 | TANK |
| 3 | MOTOR COVER |
| 4 | MOTOR BASE |
| 5 | RUBBER |
| 6 | VIBRATION SHAFT |
| 7 | SHAFT COLLAR |
| 8 | SUPPRESSOR PLATE |
| 9 | TEFLON SHEET |
| 10 | BLADE |
| 11 | SPRING BEARING |
| 12 | SPRING BEARING SPACER |
| 13 | SPRING COVER |
| 14 | ANTI-VIBRATION RUBBER (1) |
| 15 | ANTI-VIBRATION RUBBER (2) |
| 16 | BUSBAR |
| 17 | BUSBAR BEARING |
| 18 | ELECTRODE COVER |
| 19 | BUSBAR CLAMP |
| 20 | ELECTRODE PLATE (+) |
| 21 | ELECTRODE PLATE (−) |
| 22 | HOOK |
| 23 | VIBRATION MOTOR 75W 200V X3-PHASE |
| 24 | SPRING |
| 25 | RECTIFIER |
| 26 | OVERFLOW VALVE |
| 27 | DRAIN VALVE |
| 28 | FLOW METER |
| 35 | INVERTER |

END OF AUGUST 2003

BEGINNING OF JANUARY 2004

UNDILUTED FLUID
(CULTURED FOR 48 HOURS)

ELECTROLYZED FOR 1 MINUTE
(CULTURED FOR 48 HOURS)

ELECTROLYZED FOR 3 MINUTES
(CULTURED FOR 48 HOURS)

ELECTROLYZED FOR 5 MINUTES
(CULTURED FOR 48 HOURS)

NEUTRAL ELECTROLYTIC WATER, NEUTRAL ELECTROLYTIC WATER PRODUCTION METHOD AND DEVICE THEREOF

This application is a 371 of PCT/JP2005/018528 filed on Oct. 6, 2005, published on Apr. 20, 2006 under publication number WO 2006/041001 A1 which claims priority benefits from Japanese Patent Application Number 2004-296332 filed Oct. 8, 2004.

FIELD OF THE INVENTION

This invention relates to neutral electrolytic water generated from an electrolyte tank including a low-frequency vibration-stirring apparatus, and to a device for continuously producing that neutral electrolytic water.

BACKGROUND OF THE INVENTION

Oxygen and hydrogen are generated at the electrodes when electrolyzing water by means of a device with diaphragms (separator films). In that case, ion electrophoresis occurs in the fluid due to electrical attraction. An acidic substance is consequently generated at the positive electrode (anode) enclosing the film and that liquid becomes an acidic liquid. The liquid at the negative terminal (cathode) on the other hand, becomes an alkaline liquid.

In the related art, acidic water is produced at the anode, and deoxidized water is produced at the cathode by electrolysis in a 2-tank type electrolyte tank or 3-tank type electrolyte tank using electrolytic films. This electrolytic water functions as a pH (potential of hydrogen) adjuster, oxidizer, and reducer and is also utilized in a wide range of fields such as medical treatment, the electronic industry, agriculture, and the food product industry.

This type of electrolytic water is strongly acidic water or strongly alkaline water. The pH of the strongly acidic water is 2.7 or less. The pH of the strongly alkaline water is 11 or more. No germs or microorganisms can survive at these pH levels. A neutral electrolytic water whose effect is the same or better than the electrolytic water of the related art is now needed.

Technology is disclosed in patent document 1 (Japan Techno Co., Ltd.) for producing a sterilizing or germicidal effect by processing with a vibration-stirring means using anatase titanium oxide blades (vanes). In this disclosed technology, the photocatalytic effect of the blades electrolyzed organic compounds and killed germs within the water, breaking down small quantities of chlorinate compounds (organic halogen compounds such as trihalomethanes and dioxins), and oxidizing nitric acid ions in water lines and sulfuric acid in well (underground) water respectively into nitrous acid ions and sulfurous acid ions. The antiseptic fluid rendered by the technology described in that document was neutral (pH 7.5 to 7.6) and the concentration of the sulfurous ions was approximately 0.08 to 0.5 milligrams per liter. Moreover, this neutral electrolytic water was antiseptic or germ-free after the processing, however this germicidal effect could not be maintained for a long period of time. The technology disclosed in patent document 2 (Japan Techno Co., Ltd.) operated via a vibration-stirring means installed in the water tank and utilized a sterilizing (disinfecting) means such as germicidal metal/metallic compounds (photocatalytic), members generating a magnetic force or ultraviolet rays as methods to clean or sterilize food products. This method utilizes the oxidizing power of the photocatalyst to produce sterilized water by using the photocatalytic effect of the vibration-stirring device. However, the disinfecting effect did not last after the vibration-stirring device was stopped, so utilizing the sterilized water away from the equipment was difficult. The sealed sterilized water did not change until its container was unsealed. The disinfected water was therefore used along with the photocatalytic device so that the sterilizing power did not last for a long time if the equipment was the open type.

The technology in the patent document 3 discloses a method for manufacturing sterilized water with a hypochlorous acid content of 0.2 to 2 ppm by utilizing the separator film type electrolyzing tank. However, the sterilized water possessed a pH of 3 or less showing strong acidity. Therefore in addition to the above described problem, this technology had the drawback that the service life of the device was limited.

The technology in the patent document 4 (Miura Denshi Co., Ltd. and others) discloses a method for supplying saltwater to an electrolyte tank containing an anode and a cathode to produce free chlorine water. This free chlorine water is a purified and sterilized water for uses such as in foodstuffs and sanitation purposes, and contains a high content of free chlorine.

This invention is a neutral electrolytic water with no chlorine odor yet possessing a strong germicidal effect, making it effective as a disinfectant for wounds, boils, burns, athlete's foot, atopy, and as a disinfectant for bathrooms. Moreover, this neutral electrolytic water is also effective as a deodorant for people and pets, for improving oral odors, and as a skin (facial) lotion or health beverage, and for purifying foodstuffs or raising plants. Additional benefits are that the effects last for a long time, and that there is yet no other electrolytic water possessing the features of both strong alkalinity and strong acidity.

More specifically, this neutral electrolytic water contains large amount of $H_2$ and $O_2$. Furthermore there has never been an electrolytic water containing activized oxygen of OH, $D_2$, HD and HDO.

The overall size of the equipment must also be made more compact and simpler in order to promote the widespread use of neutral electrolytic water.

Patent document 1: JP-A No. 122109/2004 (Japan Techno Co., Ltd.)
Patent document 2: JP-A No. 008093/2004 (Japan Techno Co., Ltd.)
Patent document 3: International Publication No. WO96/03881 (Toto Ltd.)
Patent document 4: JP-A No. 330986/1992 (Miura Denshi Co., Ltd.)

SUMMARY OF THE INVENTION

In view of the above described problems in the related art, the present invention has the object of providing neutral electrolytic water usable in a wide range of fields and stable over long periods of time. The present invention has the further object of providing a method and device for producing that neutral electrolytic water.

The method of the present invention for producing neutral electrolytic water is characterized in including an electrolysis process that applies a voltage of 1 volt to 30 volts, and current density of 5 $A/dm^2$ to 300 $A/dm^2$ from a direct current or pulsed current, to a liquid for processing containing at least one type of salt selected from a group consisting of NaCl, KCl, and $CaCl_2$ while vibrating that liquid at an amplitude from 0.01 to 15 millimeters at a period between 10 Hertz and 200 Hertz.

The method of the present invention for producing neutral electrolytic water is characterized in that the salt concentration in the water for processing is 0.05 percent or more by weight and 10 percent or less by weight.

The method of the present invention for producing neutral electrolytic water is characterized in that the process for performing electrolysis is performed in 5 minutes or more, or 90 minutes or less.

The method of the present invention for producing neutral electrolytic water is characterized in that the water for processing is sea water.

The method of the present invention for producing neutral electrolytic water is characterized in that the water is selected from a group including tap water, underground water, well water, distilled water, soft water, ion replacement water and reverse osmosis membrane water.

The method of the present invention for producing neutral electrolytic water is characterized in further including a process for photocatalyzing the water for processing prior to the process for performing electrolysis.

The method of the present invention for producing neutral electrolytic water is characterized in that the photocatalyzing process is performed by making the water for processing come in contact with photo-activized anatase titanium oxide (blades or plates).

The neutral electrolytic water of this invention is characterized in containing a activized elements selected from a group made up of OH, $D_2$, HD and HDO.

The neutral electrolytic water of this invention is characterized in containing 1 milligram per liter or more to 7 grams or less per liter of residual chlorine.

The neutral electrolytic water of this invention is characterized in that the pH of the hydrogen ion exponent is larger than 6.5 and lower than 8.5. In typical non-separator film electrolysis methods not used along with a vibration-stirring device, an alkaline electrolytic water is obtained whose pH must be adjusted even though needed in the neutral region, however the neutral electrolytic water obtained in this invention is electrolytic water directly within the neutral region.

The neutral electrolytic water of this invention is characterized in that the oxidation-reduction potential (voltage) is higher than 650 millivolts and lower than 800 millivolts.

The neutral electrolytic water of this invention is characterized in being utilized in at least one application selected from a group including sterilization, health beverages, washing of foodstuffs, medical treatment, cosmetics, mist spray, deodorizing, rust prevention, plant growth, disinfecting, pet/animal care, pond/fountain spraying, reservoir water, water for product tasting, and purifying.

The device for producing neutral electrolytic water of this invention comprising:

an electrolyte tank for storing the water for processing, and multiple electrode plates installed alternately in proximity to the electrolyte tank, and connected to a direct current power supply by way of a rectifier, and a vibration-stirring device to make the water for processing agitate and flow, wherein the device is characterized in applying a direct current or a pulsed current to the multiple electrode plates to perform electrolyzing while vibrating the water for processing with the vibration-stirring device.

The device for producing neutral electrolytic water of this invention comprising:

an electrolyte tank for storing the water for processing, and a vibration-stirring device including multiple vibrating blades connected via a rectifier to the direct current power supply, for making the water for processing agitate and flow, is characterized in applying a direct current or a pulsed current to the multiple vibrating blades to perform electrolyzing while vibrating the water for processing with the vibration-stirring device.

The device for producing neutral electrolytic water of this invention comprising:

a photocatalyzing tank for performing photocatalysis of the water for processing, and an electrolyte tank for storing the photocatalyzed water for processing, and multiple electrode plates installed alternately in proximity to the electrolyte tank, and connected to a direct current power supply by way of a rectifier, and a vibration-stirring device to make the water for processing agitate and flow, wherein the device is characterized in applying a direct current or a pulsed current to the multiple electrode plates to perform electrolyzing while vibrating the water for processing with the vibration-stirring device.

The device for producing neutral electrolytic water of this invention is characterized in that the distance between the multiple electrodes is 0.3 millimeters to 100 millimeters.

The device for producing electrolytic water of this invention is characterized in that the distance between the multiple vibrating blades is 0.3 millimeters to 100 millimeters.

The device for producing neutral electrolytic water of this invention comprising:

a photocatalyzing tank for photocatalyzing the water for processing, and an electrolyte tank for storing the photocatalyzed water for processing, and multiple electrodes installed alternately in proximity to the electrolyte tank, and connected to a direct current power supply by way of a rectifier, and a vibration-stirring device to make the water for processing agitate and flow, wherein the device is characterized in applying a direct current or a pulsed current to the multiple electrode plates to perform electrolyzing while vibrating the water for processing with the vibration-stirring device.

A device for producing neutral electrolytic water of this invention is characterized in that the vibration-stirring unit is an insulated type vibration-stirring device.

A device for producing neutral electrolytic water of this invention is characterized in that the liquid for processing contains at least one type of salt selected from a group consisting of NaCl, KCl, and $CaCl_2$.

The vibration-stirring device in this invention signifies a low-frequency vibration-stirring device. In other words, an agitator device containing an agitating shaft vibrating between 10 Hertz to 200 Hertz by driving a vibration motor from an inverter to make blades attached to multiple levels on the agitating shaft vibrate within a few centimeters to generate a turbulent flow at a low energy.

The insulated type vibration-stirring device refers to a device connecting the agitating shaft of the vibration-stirring device, or utilizing the vibrating blades attached to that shaft as electrodes. Utilizing this insulated type vibration-stirring device in the electrolyte tank eliminates the need for electrode plates that are normally required, since this device incorporates the functions of the electrode plates.

THE EFFECT OF THE INVENTION

The neutral electrolytic water of this invention possesses characteristics superior to either of already existing acidic electrolytic water or alkaline electrolytic water, and may be utilized for sterilizing, in health beverages, for washing of foodstuffs, in medical treatment, in cosmetics, in mist spray, for deodorizing, for rust prevention, for plant growth, for disinfecting, for pet/animal care, for pond/fountain spraying, in reservoir water, in water for product tasting, and for purifying. Moreover, those characteristics remain stable over a long period from six months after storage to one year or longer. Also this neutral electrolytic water has no chlorine smell.

This invention provides a neutral electrolytic water stable over long periods of time, and further provides a compact sterilizing water production device or automatic sterilizing water production device.

BRIEF DESCRIPTION OF THE DRAWINGS

FIG. 5 is a parts list table for the water electrolyzing device of the first embodiment;

Figure 1:
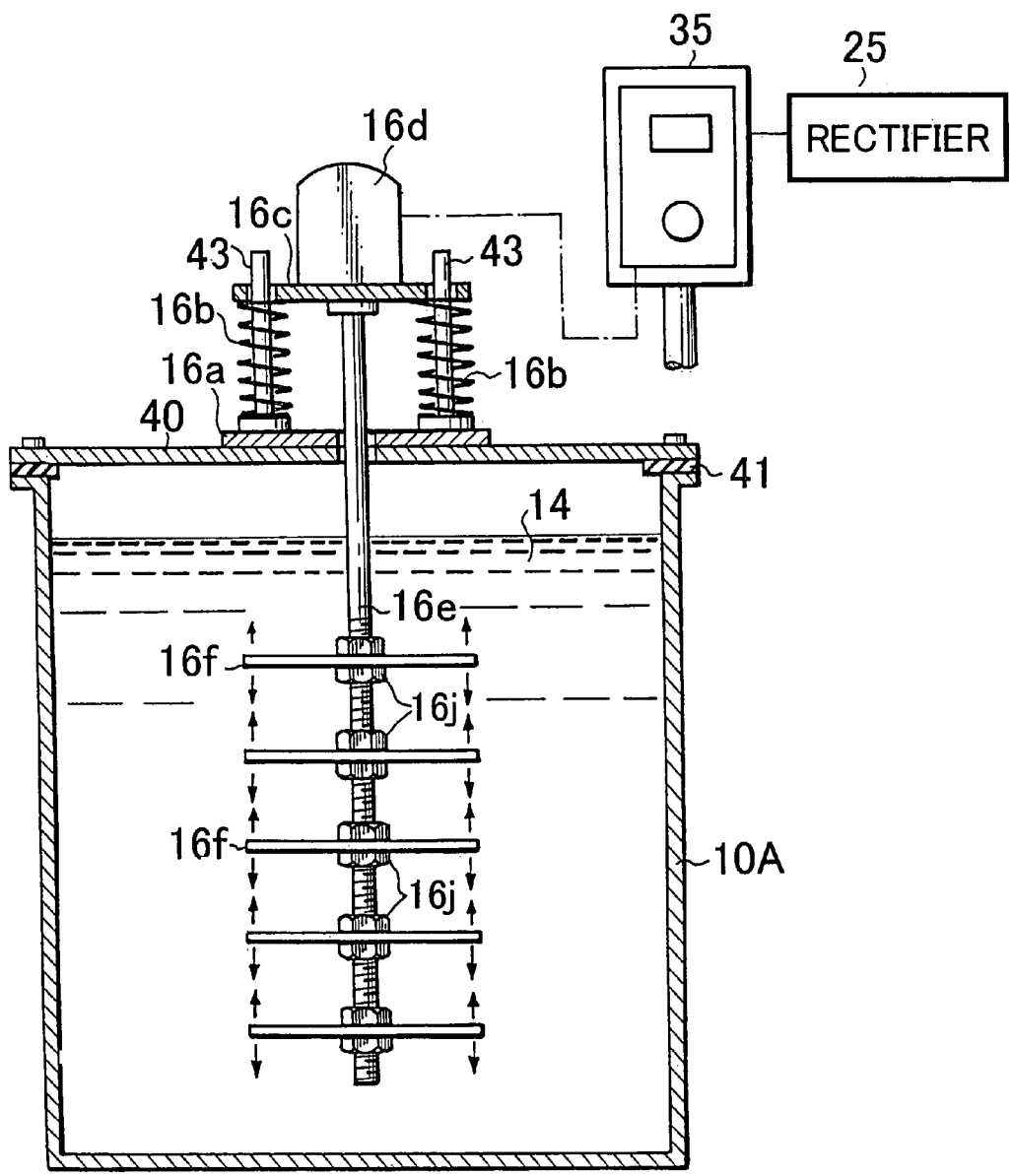
FIG. 1 is a drawing showing an overview of the vibration-stirring means of the present invention.

EXPLANATION OF REFERENCE NUMERAL 1 water tank
2 vibration motor
3 spring
7 vibrating rod
8 vibrating blade
8' electrode
9 vibrating blade clamping member and/or electrode clamping member
10 vibrating blade
11 connecting section
14 water for processing
16 insulation type vibration-stirring device
16a base plate
16b coil spring
16c joint vibrating member
16d vibration motor
16e vibrating rod
16f vibrating blade
16j nut
20 electrode plate
21 electrode plate
23 vibration motor
27 wire
30 spacer
33 composite resin
34 power supply
35 transistor-inverter
40 installation stand
41 vibration cushion material
43 guide member
81 electrode (+)
82 electrode (−)
83 insulation member
84 insulation member
136 power supply

DETAILED DESCRIPTION OF THE PREFERRED EMBODIMENTS

The present invention is described according to the following embodiments, however this invention is not limited by these examples.

The neutral electrolytic water production device of this invention includes the following structural elements.

1) The electrolyte tank contains a vibration-stirring device, and includes an anode and a cathode. The electrolyte tank may be a type that electrolyzes by utilizing the vibrating blades as electrode plates.

2) The material for the anode may include gold, rhodium, and platinum, etc. These materials may be used singly or these materials may be used as an alloy surface treated with an electrically conductive material.

3) The material for the cathode may include stainless steel and titanium, etc. These materials may be used singly or these materials may be used as an alloy surface treated with an electrically conductive material.

4) The electrolyte tank includes a supply port for constantly draining the overflow of neutral electrolytic water and for supplying water.

5) A direct current power supply required for electrolysis.

6) A salt water tank for supplying salt water for electrolysis (Volume capable of continuous supply for a minimum of three days at concentration for 1 to 10 percent, and with a low water level sensor alarm function.)

7) A supply pump for continuously supplying a specified amount of electrolytic water.

8) An air blower for supplying liquefied salt solution to within the electrolyte tank.

9) The water for processing contains water and at least one type of salt selected from a group consisting of NaCl, KCl, and $CaCl_2$. This water includes tap water, underground water, well water, distilled water, soft water, ion replacement water and reverse osmosis membrane water. The water may also include swimming pool water and bath water.

The neutral electrolytic water is produced by electrolyzing using a non-separator film electrolyte tank containing a vibration-stirring device and multiple electrode plates or an insulated type vibration-stirring device with vibrating blades serving as electrode plates. The vibration-stirring device is explained here in detail (one type of vibration-stirring means).

FIG. 1 is drawing showing a concept view of the vibration-stirring means. In this example, a base plate 16a is clamped to the installation bed 40 on the upper part of the electrolyte tank 10A by way of the vibration absorbing member 41. A rod-shaped guide member 43 extending perpendicularly upwards is clamped to the installation bed 40. This guide member 43 is installed (positioned) within the coil spring 16b. An inverter 35 for controlling the frequency of the vibration motor 16d is installed between the vibration motor 16d and the rectifier 25 for driving that motor 16d. The voltage of the rectifier 25 is for example 200 volts AC.

The vibration-stirring means of the present invention is not limited to that shown in FIG. 1, and may for example be used in the inventions disclosed in Japanese patent publication 1941498, Japanese patent publication 2707530, Japanese patent publication 2762388, Japanese patent publication 2852878, Japanese patent publication 3142417, JP-A No. 339270/2003, JP-A No. 282669/2002, JP-A No. 210341/2002, JP-A No. 191680/2002, JP-A No. 102323/2002, JP-A No. 271189/2001, JP-A No. 122109/2004, JP-A No. 055747/2002, WO 03/000395 A1 and WO 02/090621 A1, etc.

The vibration-stirring means of this invention is described next in further detail. An inverter oscillates the vibration motor 16d at 10 to 500 Hertz. This vibration is conveyed to the vibrating rod 16e, and the vibrating blade 16f is made to vibrate under conditions of an amplitude of 0.01 to 30.0 millimeters as well as a frequency of 500 to 30,000 revolutions per minute.

A Uras Vibrator (Murakami Seisakusho) low frequency vibration motor (50 hertz to 60 hertz) and a Haifre Uras (Murakami Seisakusho) high-frequency vibration motor (60 Hertz to 200 Hertz) are used as the vibrating elements.

The anode (positive electrode) is preferably an anode plate of stainless steel (SUS) plate or titanium plate covered with platinum or vanadium in view of the required characteristics such as (1) no flow of hazardous metallic ions, (2) corrosion resistance, (3) low chlorination over-voltage, (4) large oxygen over-voltage. The anode plate is preferably Pt—Ir alloy covered with platinum, or titanium alloy plate.

The cathode (negative electrode) plate is preferably made from a negative electrode member including rhodium, nickel, nickel alloy (Ni—$Mo_2$, Ni—Co, Ni—Fe, Ni—Mo—Cd, Ni—S), titanium alloy.

The mutual gap between the electrodes is 60 millimeters or less and is preferably 0.2 to 5 millimeters. Shortening this distance increases the production of neutral electrolytic water and prevents heat emissions. However when this distance is shortened, a stoppage in the electrolytic water vibration must be stopped in order to prevent burning or scorching the electrodes. Using the vibration-stirring device allows efficient production and neutral electrolytic water with a powerful germicidal effect and no chlorine smell can be obtained.

The electrolyte tank of this invention can be the so-called non-separator film type that does not contain separator film within the tank. The inner surface of the electrolyte tank of the related art was covered with a non-corrosive resin to make it able to withstand heat and to prevent corrosion. However there is virtually no need for this resin cover in the present invention. Maintaining the separator film during electrolyzing raises costs and the electrical conductivity becomes poor.

The salt liquefied into the water was described as at least one type of salt selected from a group consisting of NaCl, KCl, and $CaCl_2$. The salt concentration in the water for processing is 0.05 percent or more by weight and 10 percent or less by weight. NaCl is used in this embodiment, but the same effect has been confirmed from KCl and $CaCl_2$. Also these can be used together. Seawater mostly contains NaCl and KCl, and so is included in this invention as a water for processing.

The method for producing neutral electrolytic water in this invention normally performs the electrolyzing in a period from 5 to 90 minutes. In other words, electrolyzing is performed using the water for processing and applying a direct current or pulsed current, and maintaining the voltage within a range normally from 1 to 30 volts, and further maintaining the current density within a range from 5 to 300 A/$dm^2$.

Usually $H_2$ and $O_2$ are emitted as a gas during electrolyzing of water. However, in this invention a vibration-stirring device is operated so that the generated gas and the $H_2$ and $O_2$ disperse and liquefy within the water, and little gas exits outside the device.

A pulsed current is more preferable than direct current. The pulsed current preferably has a pulse waveform and a rectangular pulse waveform is particularly preferable. A pulsed waveform prevents crystallization, allows long-term use, and prevents a drop in performance.

This pulsed waveform is generated by technology of the known art. Examples of such technology include: a transistor regulated power supply, a dropper type power supply, a switching power supply, a silicon rectifier, an SCR type rectifier, a high-frequency (RF) rectifier, and an inverter digital-controller rectifier.

The neutral electrolytic water of this invention is produced as described above. Namely the neutral electrolytic water is characterized in containing large quantities of $H_2$ and $O_2$ and also activized components made up of activized oxygen OH, $D_2$, HD and HDO. This neutral electrolytic water contains hypochlorous acid and chlorous acid ions. The residual chlorine content is 1 milligram to 7 grams per liter.

In the neutral electrolytic water of this invention the pH of the hydrogen ion exponent is larger than 6.5 and lower than 8.5 ($6.5 < pH < 8.5$), and preferably is larger than 6.5 and lower than 7.5. Therefore the neutral electrolytic water of this invention is not acidic or alkaline water, but is a neutral electrolytic water.

The acidic electrolytic water of the related art exhibits a strong sterilizing (or germicidal effect. However in spite of the fact that the neutral electrolytic water of this invention is neutral, it retains the germicidal effect (or sterilizing power) over a long period, so that the germicidal effect can be maintained far in excess of that acid electrolytic water of the related art.

The neutral electrolytic water of this invention is generally used with a residual chlorine content within the following range. The residual chlorine content increases as the electrolyzing continues so the device operating time might have to be adjusted according to the application.

| Skin use | 15 to 20 ppm |
|---|---|
| Bath use | 100 ppm (approx.) |
| Deodorizing-sterilizing use | 300 ppm (approx.) |

The method for measuring the above residual chlorine content conforms to JIS (Japanese industrial standards) K0102 for tap water.

The neutral electrolytic water of this invention possesses anti-bacterial, bacteria-suppressant, and germicidal effects on microorganisms of all types. This neutral electrolytic water is also effective against the following bacteria; colon bacillus (colon bacillus, Escherichia coli bacillus sources such as O-157), Salmonella, Enteritis vibrio, campylobacter•Yersinia, Clostridium perfringens, Non-agglutinate vibrius, Enterococcus, Psudomonas aeruginosa, Burkholderiacepacia, Staphylococcus aureus, Staphylococcus epidermis, Streptococcus pneumonia, Serratia, proteus, Enterobacter, citrobacter, Entercocous, Klebsiella, Bacteroides, Legionella, Mycobacterium, pneumocystiscarinii, fungus, and virus-causing germs.

Using the neutral electrolytic water of this invention may render a germicidal (sterilizing) effect from several dozen minutes to several days.

Applications of the neutral electrolytic water of this invention also include the following.

1) Deodorizing and sterilizing of the interior of hospital and facilities for the elderly
2) Deodorizing and sterilizing of the inside of hotels, restaurants, coffee shops and cafeterias
3) Deodorizing and sterilizing of the meeting places with many people and pachinko halls
4) Deodorizing and sterilizing of the inside of bars and restaurants
5) Sterilizing the inside of general practitioner's treatment rooms
6) Oral disinfection for dentist's office and home use
7) Facial spray using neutral electrolytic water (Water from the spray penetrates into pores and skin layers and since negative ions come from this facial spray it is considered good for the health.)
8). Deodorizing of pets/animals, deodorizing excreta
9) Sterilizing and care of plants
10) Preventing decay in fruits and vegetables and maintaining freshness
11) Preventing halitosis and deodorizing
12) Sterilizing instruments used in hospitals
13) Preventing mold from occurring
14) Sterilizing storage tanks, water tanks for aquariums, and spray fountain water
15) Sterilizing ponds at golf courses The neutral electrolytic water of this invention is further utilized for sterilization, health beverages, washing of foodstuffs, medical treatment, cosmetics, mist spray, deodorizing, plant growth, preventing decay, disinfecting, pet/animal care, pond/fountain spraying, reservoir water, water for aquariums, and purifying.

First Embodiment

FIG. 2, FIG. 3, FIG. 4 and FIG. 5 are frontal drawings, plan (flat) views, side views and parts list tables showing the overall test device.

(1) Hydroelectrolysis Device (a) Utilized an a-Torino water production device Model 1 (30 liters) (made by Japan Techno Co., Ltd.)
Vibration motor: 75 watts 200 volts×3φ
Vibrating blades: stainless plates 4 plates SUS304
Vibration shaft: stainless rod 2 rods SUS304

(b) Electrolyte tank
Utilizing a 30 liter container covered with heat-resistant propylene resin: 500×290×305 (unit: mm)

(c) Electrodes
Anode plates: titanium mesh 3 plates (covered with platinum plating)
Cathode plates: SUS304 4-plates
Electrode gap: 20 mm
The anode plate and cathode plate are alternately installed in mutual proximity. The surface area of the electrode plates was 12 $dm^2$ for the three anode plates; and 16 $dm^2$ for the four cathode plates.

(d) Rectifier (transistor type)
Chuo Seisakusho (Corp.) PEM11-12V-200

(e) Inverter: Fuji Electric (Inc.) Product name Fuji Inverter FVR-E9S (2) Electrolytic Water
Salt (class 1 chemical product) was liquefied into water from the Tokyo metropolitan water supply (tap water), and at a salt (NaCl) content of 5 grams per liter.

(3) Vibration Flow
A direct current of 15 amperes and 12 volts was obtained from a rectifier using 3-phase 200 volts AC. The vibration frequency of the vibration motor was adjusted to 45 Hertz by the inverter, and the electrolytic water vibrated and made to flow for six minutes. The electrical current density was 2 amperes per liter.

(4) Bacteria Type
Colon bacillus (Kanto Chemical Co., Ltd.: No. ATCC8739)
Staphylococcus aureus (Kanto Chemical Co., Ltd.: No. ATCC25923)

(5) Measurement Method
The neutral electrolytic water obtained in this way was filled into bottles, stored in a cool, dark location, and measured after a one week period.
Device: Milliflex Vacuum Filtration Systems
Cultivation:
Colon bacillus MXLM Col 20 (fluid culture medium for Colon bacillus)
Staphylococcus aureus MXSM CTT24 (agar medium)
Culturing time 48 hours

TABLE 1

| Bacteria type | Processing | 0-Minutes | 2-Minutes | 4-Minutes | 8-Minutes | 10-Minutes | 30-Minutes |
|---|---|---|---|---|---|---|---|
| *Colon bacillus* *E. coli.* JCM 1349 | Vibration flow | $4.8 \times 10^7$ | Not-detected | Not-detected | Not-detected | Not-detected | Not-detected |
| | No stirring | $4.5 \times 10^7$ | $6.9 \times 10^6$ | $5.7 \times 10^4$ | $7.8 \times 10^3$ | $6.7 \times 10^2$ | Not-detected |
| *Staphylococcus aureus* JCM 2413 | Vibration flow | $3.7 \times 10^7$ | Not-detected | Not-detected | Not-detected | Not-detected | Not-detected |
| | No stirring | $3.8 \times 10^7$ | $2.9 \times 10^5$ | $2.9 \times 10^4$ | $5.6 \times 10^3$ | $4.8 \times 10^2$ | Not-detected |
| *Colon bacillus* *E. coli.* O157 | Vibration flow | $2.8 \times 10^6$ | Not-detected | Not-detected | Not-detected | Not-detected | Not-detected |
| | No stirring | $2.5 \times 10^6$ | $5.9 \times 10^5$ | $3.8 \times 10^3$ | $3.2 \times 10^2$ | $5.3 \times 10^1$ | Not-detected |

The above described sample fluid was next filled in bottles (transparent 300 milliliters) and stored for a six month period. The germicidal effect was then retested.

The electrolytic water showed almost no germicidal effect if the vibration-stirring device was not operated. An approximate 10 percent reduction in effect was observed when the vibration-stirring device was operated (45 to 50 Hertz) but the initial germicidal effect was maintained. The vibration-stirring device was not of practical use when the gap between the vibrating blades was 20 millimeters and the blades could not be made any closer to each other. Immediate use of acetic electrolytic water after adjustment is generally compulsory.

In this embodiment the batch method was used rather than an automatic production device.

If electrolyzing was accomplished by operating the vibration-stirring device then the electrolyzing process was able to proceed without raising the temperature of the electrolytic water. However if the vibration-stirring device was stopped then the temperature of the electrolytic water rose and the electrolyzing efficiency declined.

(6) Physical Data on the Neutral Electrolytic Water

The hypochlorous acid was measured by using the following method. The same measurement method was utilized in the following examples.

Purity Test (1) Liquid strong acidity hypochlorous acid solution pH2.7 or less

Weak acidity hypochlorous acid solution pH5.0 to 6.5

(2) Evaporation residual matter 0.25% or less

After twenty grams of this product was weighed and then made to evaporate, it was dried for 2 hours at 110° C., and the mass of the residual matter (minerals) then weighed. The measured value was 0.05%.

Quantitative Method (1) The strong acidic hypochlorous acid solution was measured by the following method.

Approximately twenty grams of this product was precisely weighed, and 2 grams of potassium iodide and 10 milliliters of acetic acid (1→4) was added, promptly sealed and stored in a dark location and left standing for a 15 minute period, and the separated iodine dripped by sodium thiosulfate solution at 0.01 mol per liter (starch reagent as the indicator chemical). A separate dummy test was made and correction performed.

0.01 mol per liter of sodium thiosulfate solution 1 milliliter=0.35453 milligrams Cl (2) The weak acidic hypochlorous acid solution was measured by the following method.

Approximately two hundred grams of this product was precisely weighed, and 2 grams of potassium iodide and 10 milliliters of acetic acid (1→4) was added, promptly sealed and stored in a dark location and left standing for a 15 minute period, and the separated iodine dripped by sodium thiosulfate solution at 0.005 mol per liter (starch reagent as the indicator chemical). A separate dummy test was made and correction performed.

0.005 mol per liter of sodium thiosulfate solution 1 milliliter=0.17727 milligrams Cl Hypochlorous acid content: Shown in Table 4 along with results for the second embodiment.

Residual chlorine content: 10 ppm

Figure 6:
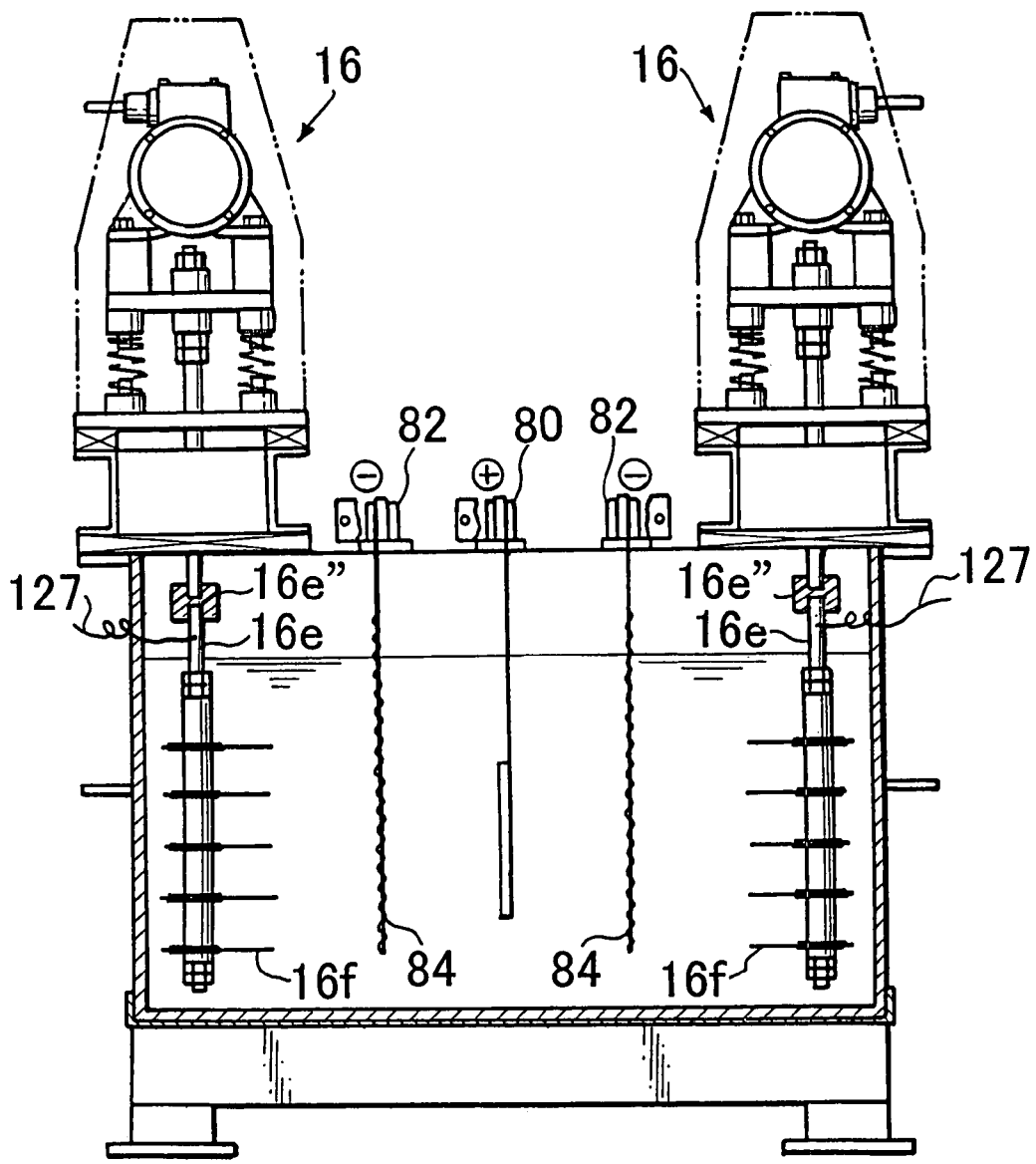
FIG. 6 is a drawing is an example of a frontal view of the water electrolyzing device of the second embodiment.
Figure 7:
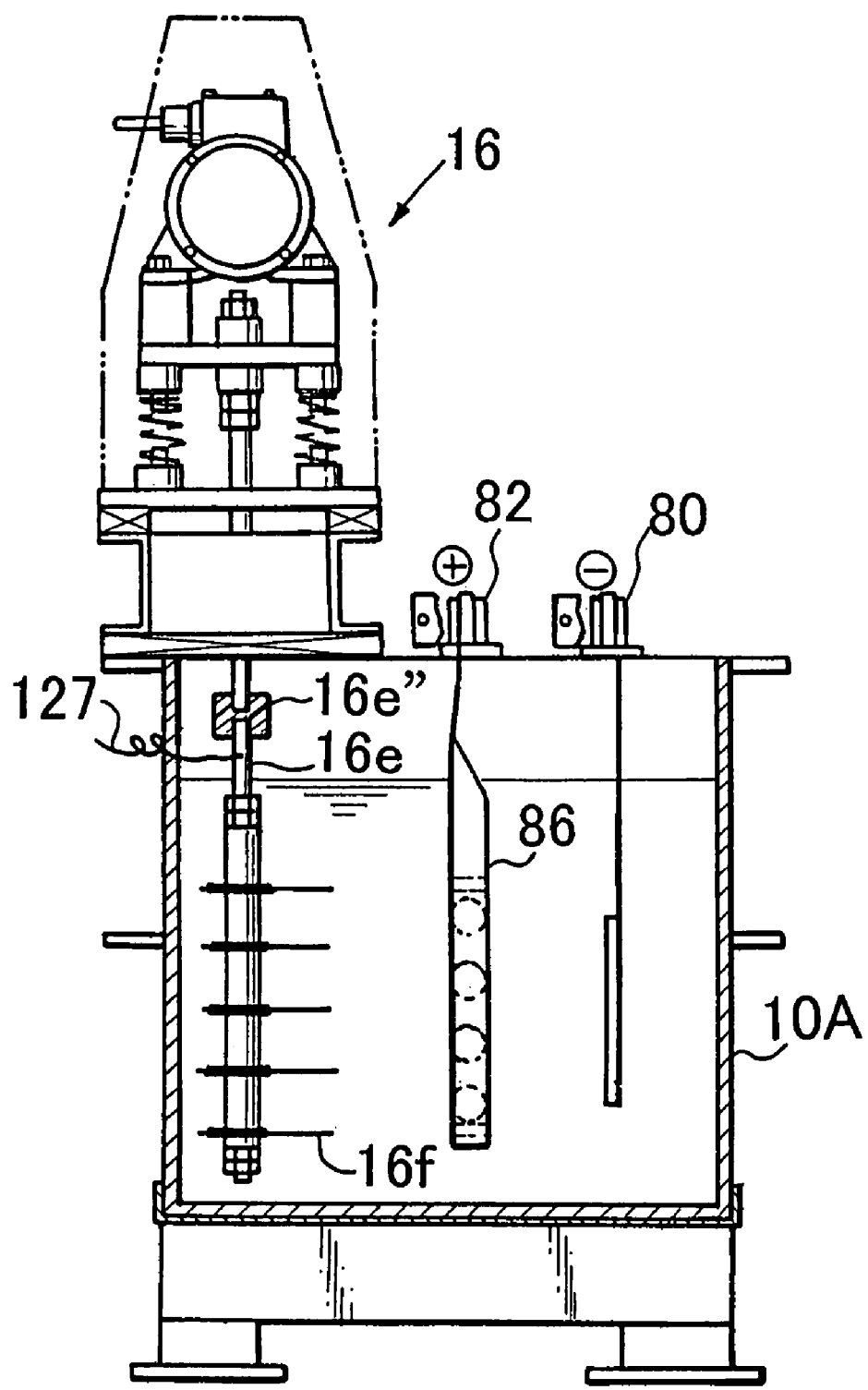
FIG. 7 is a drawing of another example of a frontal view of the water electrolyzing device of the second embodiment.

When the neutral electrolytic water produced the same as above using (100 liter: a-Torino water production device Model 2) the device of FIG. 6 and FIG. 7 and those results evaluated, essentially the same results were obtained. Hereafter, the description utilizes the reference numerals of FIG. 6 and FIG. 7 that utilizes the insulated type vibration-stirring device.

| | |
|---|---|
| 16 | insulated type vibration-stirring device |
| 16f | vibrating blade |
| 80, 82 | holding means |
| 84 | electrode member |
| 127 | electrical line |

Second Embodiment

Germicidal Test (1) Hydroelectrolysis Device

Figure 2:
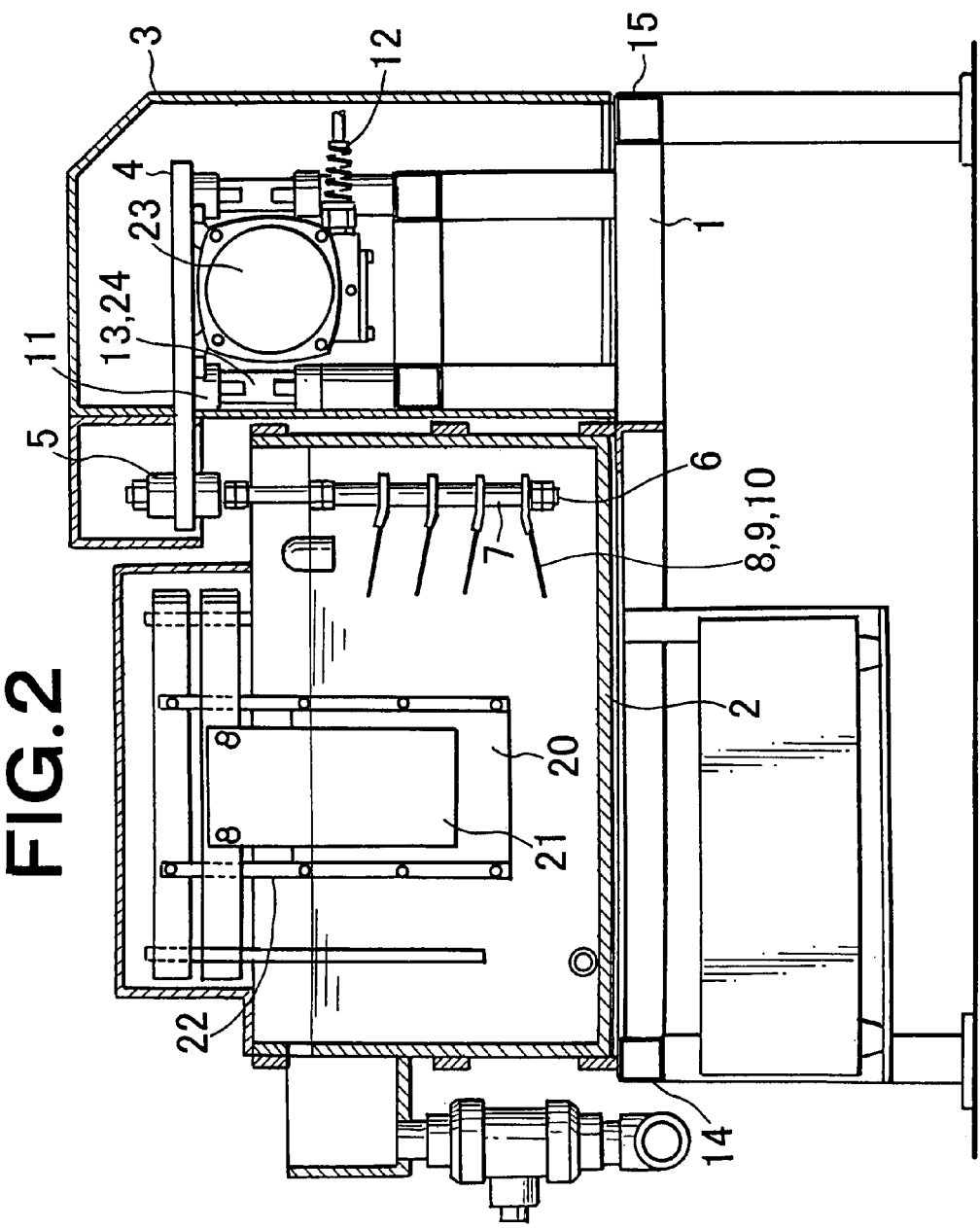
FIG. 2 is a drawing showing a frontal view of the water electrolyzing device of the first embodiment.
Figure 3:
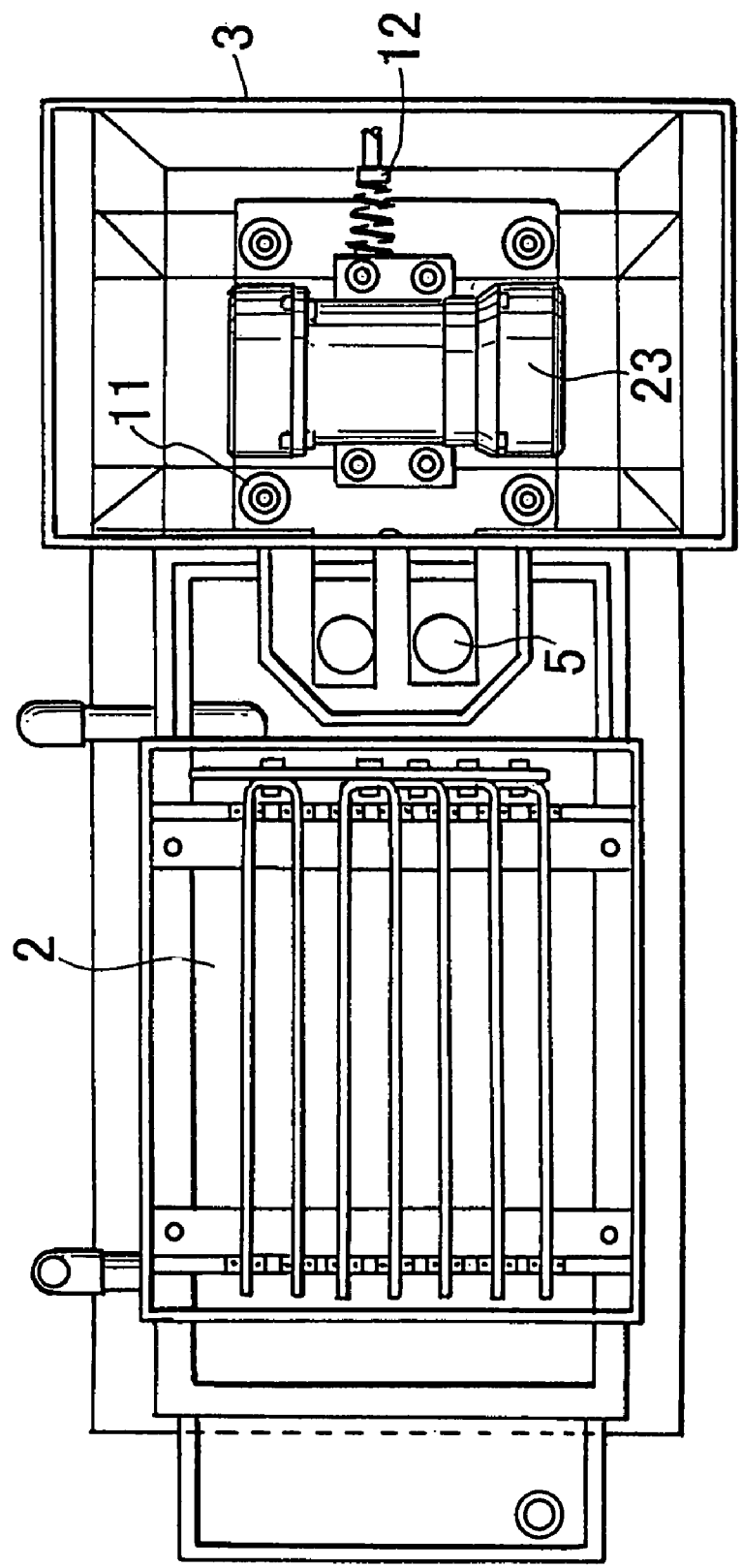
FIG. 3 is a drawing showing a plan (flat) view of the water electrolyzing device of the first embodiment.

This was a larger device than that of the first embodiment. FIG. 2 shows an overview of the (Neutral electrolytic water production device—Model 2 100 liter: a-Torino water production device Model 2) device.

Figure 8:
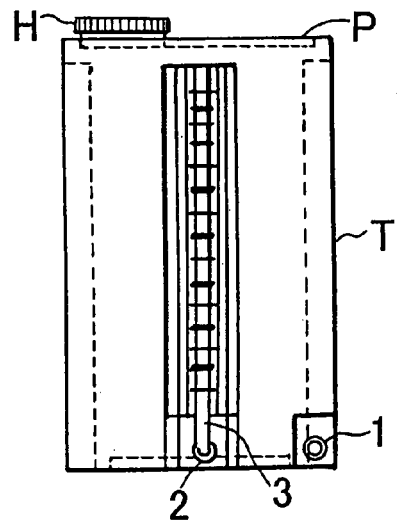
FIG. 8 is a drawing showing a frontal view of the tank in the second embodiment.
Figure 9:
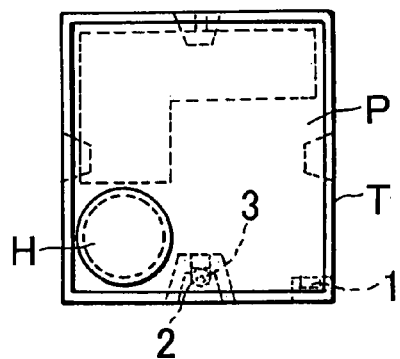
FIG. 9 is a drawing showing a plan view of the tank in the second embodiment.
Figure 10:
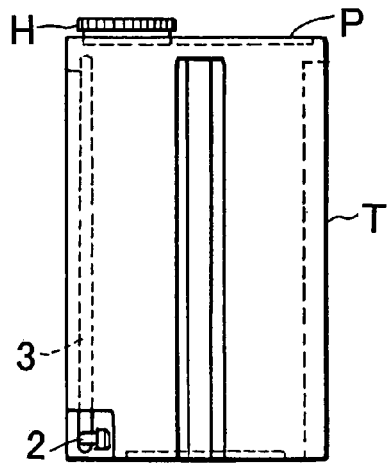
FIG. 10 is a drawing showing a side view of the tank in the second embodiment.

The vibration-stirring device is used in FIG. 2. A large-size chemical fluid tanks (auxiliary liquefier tank, 200 liters) was attached to the device. Drawings of the tanks are shown in FIG. 8 through FIG. 10.

All other conditions, namely the (2) water for processing, (3) vibration flow, (4) bacteria types, and the (5) measurement methods were the same as the first embodiment.

The germicidal test was performed in compliance with JIS-K 0102-72.2 and the number of general dead bacteria (each type) and the number of colon *bacillus* germs were measured.

TABLE 2

Germicidal test results for *colon bacillus*

| | Time | | | | | |
|---|---|---|---|---|---|---|
| | 0-Minutes | 1-Minute | 3-Minutes | 5-Minutes | 10-Minutes | 20-Minutes |
| Germ count | $3.1 \times 10^7$ | Not-detected | Not-detected | Not-detected | Not-detected | Not-detected |

TABLE 3

Germicidal test results for *staphylococcus aureus*

| | Time | | | | |
|---|---|---|---|---|---|
| | 0-Minutes | 1-Minute | 3-Minutes | 5-Minutes | 10-Minutes | 20-Minutes |
| Germ count | $1.9 \times 10^8$ | Not-detected | Not-detected | Not-detected | Not-detected | Not detected |

The above sample was next stored in a cool, dark location for a three month period. The same germicidal test as above was performed using this sample. The pulse power supply utilized 3-phase 200 volts (Chuo Seisakusho (Corp.) Rectifier Power Master PND-1).

Electrolytic water obtained from the conventional 3-chamber type electrolyte tank was tested as a comparison example. However after storage for three months there was absolutely no germicidal effect.

Neutral electrolytic water was continually produced for one month using the device of the second embodiment. Unlike the case of the first embodiment, the gap between the electrodes was set to 5 millimeters and the production yield increased 4-fold (four times).

Scorching and burns occurred when the electrode gap was set to 5 millimeters without operating the vibration-stirring device, and continuous operation was not possible.

A device to liquefy the salt beforehand was added, and neutral electrolytic water then continually produced. Continuous production was now possible over a long time period. There was no rise in the liquid temperature, and a uniform neutral electrolytic water was produced in large quantities.

Figure 4:
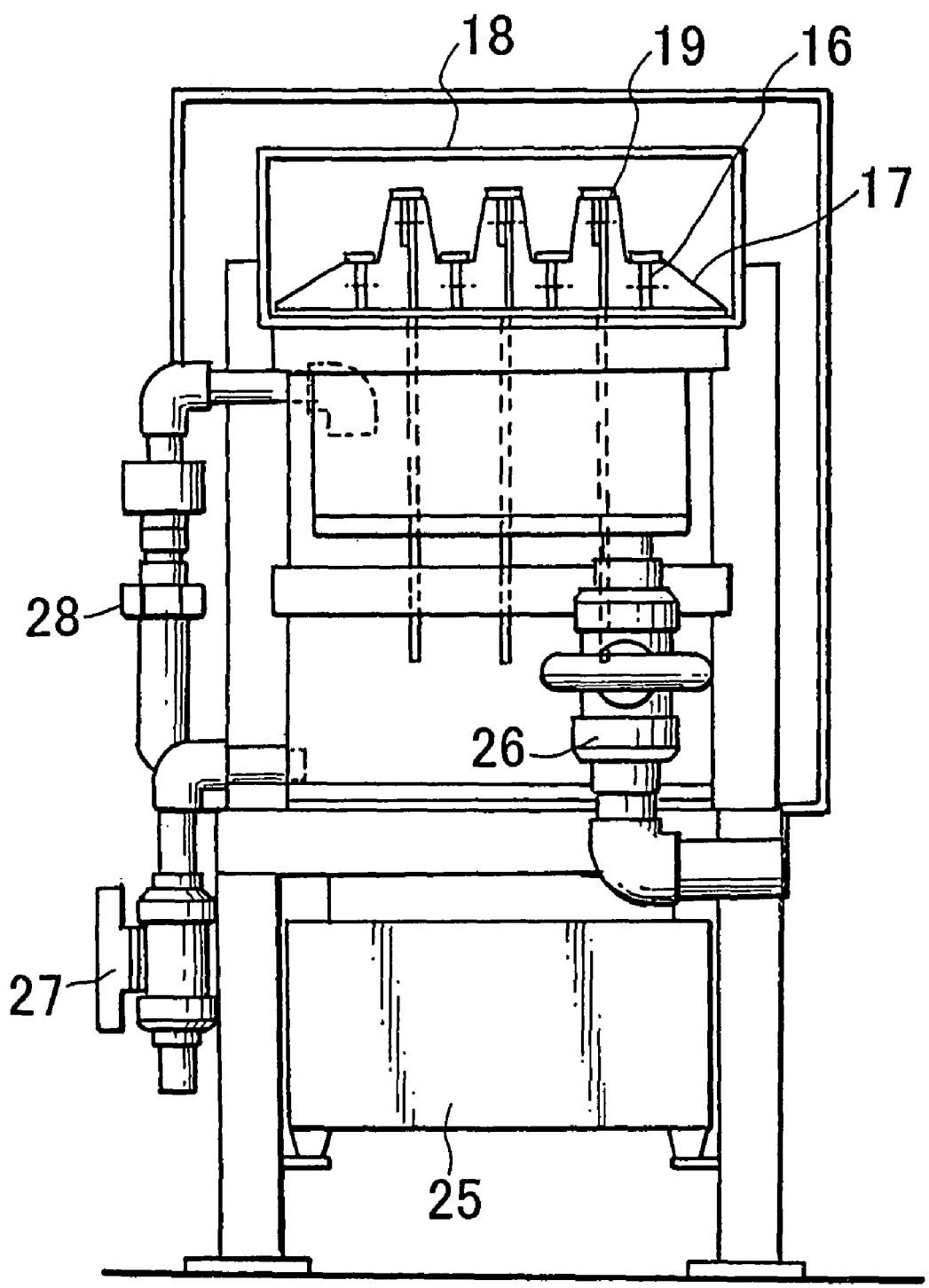
FIG. 4 is a drawing showing a side view of the water electrolyzing device of the first embodiment.

Quantizing measurements were made of the hypochlorous acid in the neutral electrolytic water obtained in the first embodiment and the second embodiment. The measurement results are shown in FIG. 4. The hypochlorous acid content in the neutral electrolytic water of both embodiments was found to be lower than that of separator film electrolytic water (strongly acidic electrolytic water).

Hypochlorous acid content in the separator film electrolytic water: 5 ppm

TABLE 4

Hypochlorous acid content

| | Directly afterwards | After 1 week | After 1 month |
|---|---|---|---|
| First embodiment | 2 ppm | 2 ppm | 1 ppm |
| Second embodiment | 2 ppm | 2 ppm | 1 ppm |

The above results confirm that like alkaline electrolytic water, the neutral electrolytic water of this invention can be used in items such as mouthwash (gargling) and skin lotion.

Tap water was continuously electrolyzed per the first embodiment and the second embodiment and the neutral electrolytic water of this invention was obtained. This neutral electrolytic water was sealed in bottles and stored for about a one week period. The gas emitted from the neutral electrolytic water was then sampled and analyzed. Elements of the emitted gas were $H_2$, $O_2$, $H_2O$, OH, $D_2$, HD and HDO. The activized elements among these were OH, $D_2$, HD and HDO. No significant differences were found between the two types.

Figure 11:
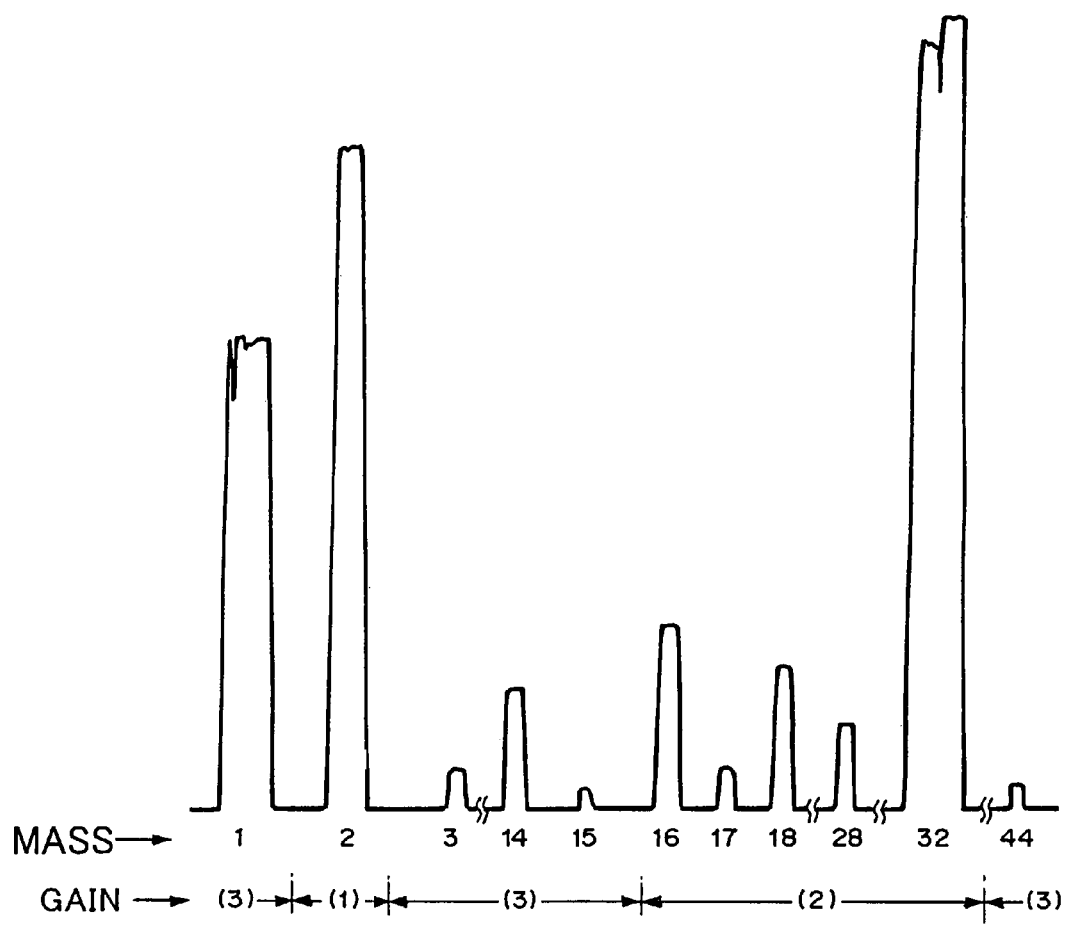
FIG. 11 is a drawing showing an example of the analysis flow chart for the gas that is generated (raw gas)

An example of the analysis chart of the raw gas that was emitted is shown in FIG. 11.

In FIG. 11, the horizontal axis shows the mass number of the observed molecule while the vertical axis shows the intensity. In the GAIN indicated in the figure, (1) indicates a height for the mass 100 times the actual height, while (2) indicates a height for the mass 10 times the actual height, and (3) indicates the actual height for the mass. In other words, the quantity for the applicable gas element is small so the mass for GAIN (1) and GAIN (2) shows it was amplified.

Approximate figures for element ratios of the emitted gases are shown next.

$H_2$: 55 to 70 mol %
H, 0.12 to 0.45 mol %
$^3$H and/or HD 0.3 to 1.2 mol %
OH: 0.3 to 1.2 mol %
$^{16}$O: 1.0 to 4.2 mol %
$O_2$: 5 to 27 mol %

The mass spectrometer used here for analysis (dual-convergence) [product brand name EMD-O5SK] was made by the Electronic Science Co., Ltd. Analysis conditions were as follows.

Ion acceleration speed: 1200 volts
Ionization method: voltage accelerated impact type
Resolution: 500
Ion flight distance: 26 cm
Vacuum intensity: 5'10-7 Torr
Full scale: 5 volts
(6) Other Physical Data for the Neutral Electrolytic Water
Residual chlorine content: 15 ppm Third Embodiment (1) Hydroelectrolysis Device (Small Model)

Figure 12:
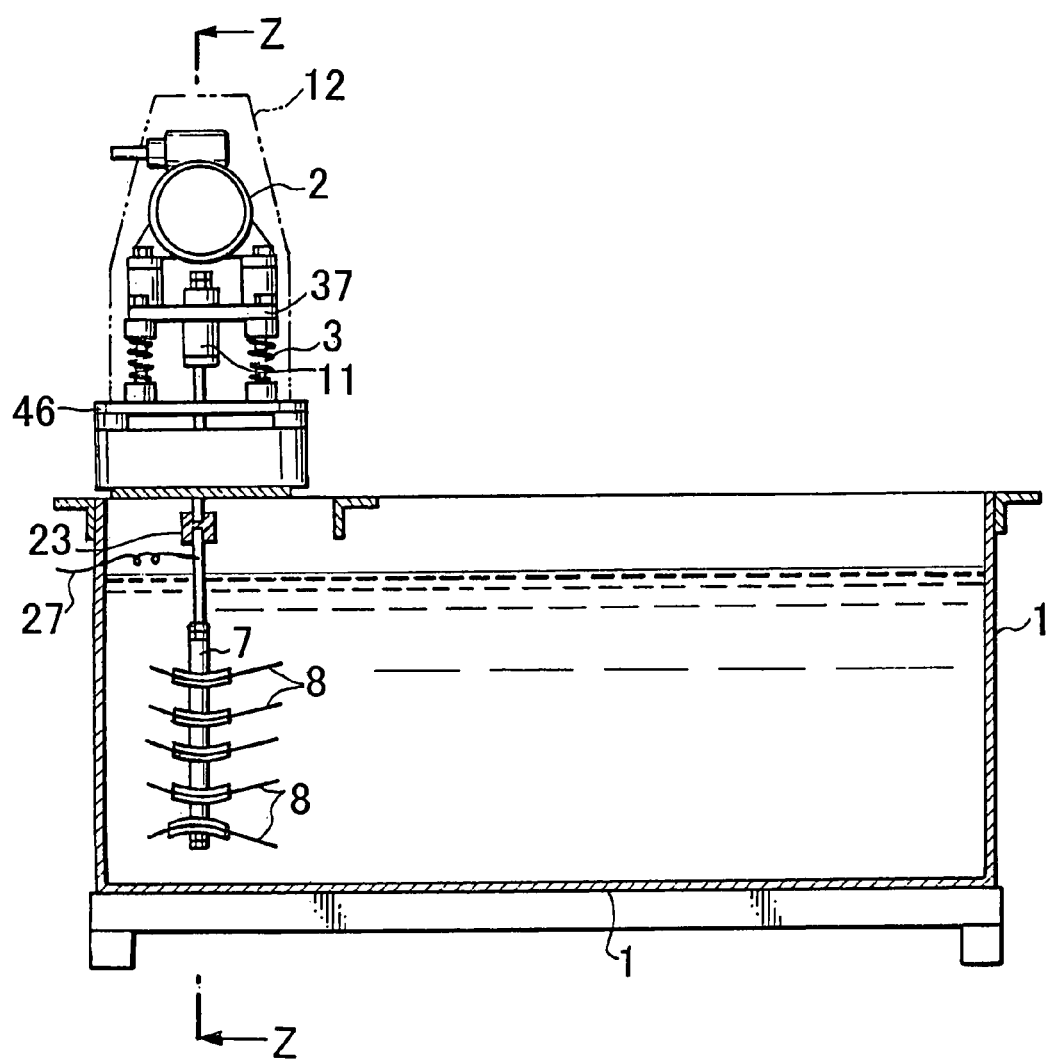
FIG. 12 is a drawing showing a frontal view of the water electrolyzing device of the third embodiment.
Figure 13:
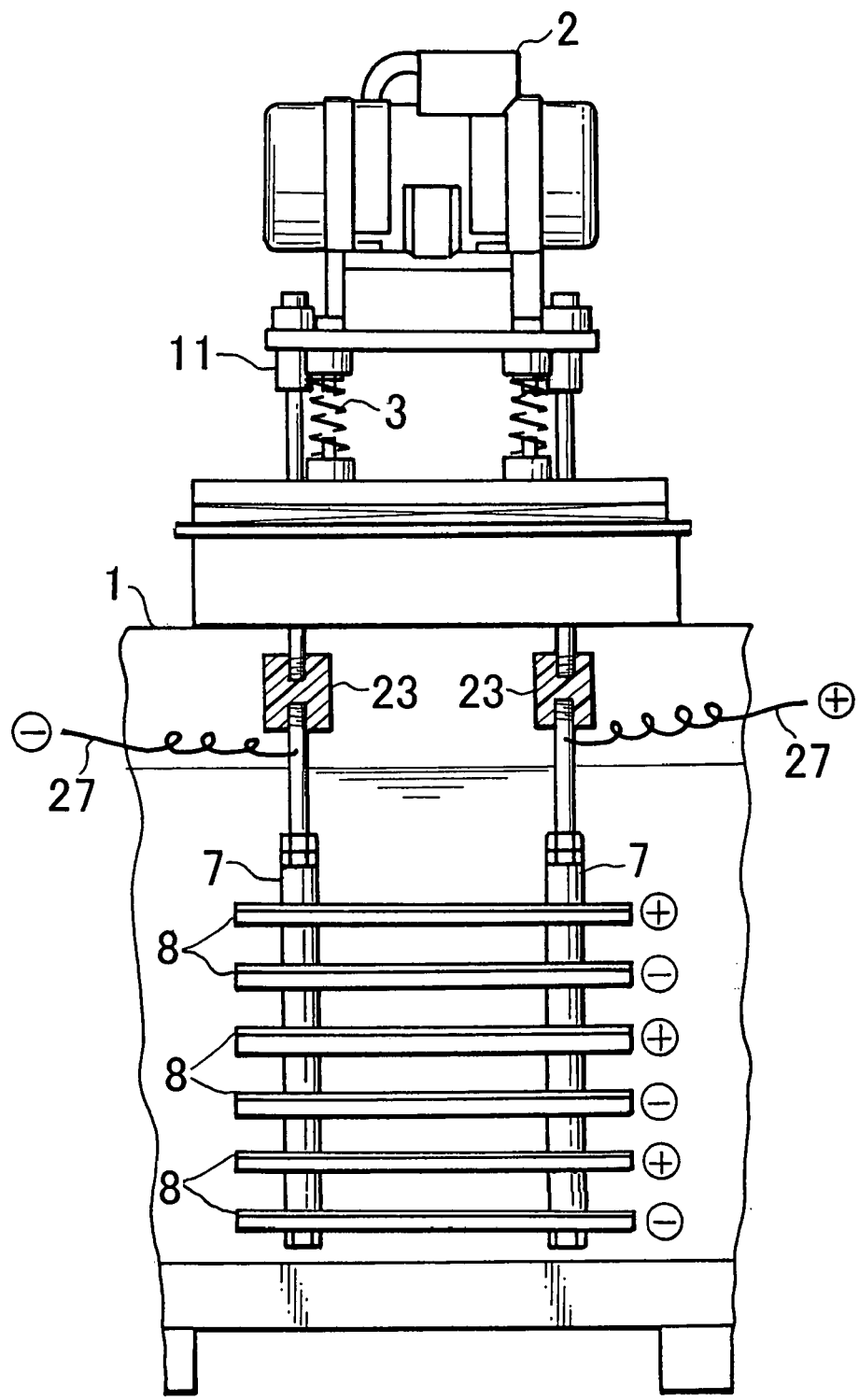
FIG. 13 is drawing showing an example of the vibrating blade placement in the third embodiment.
Figure 14:
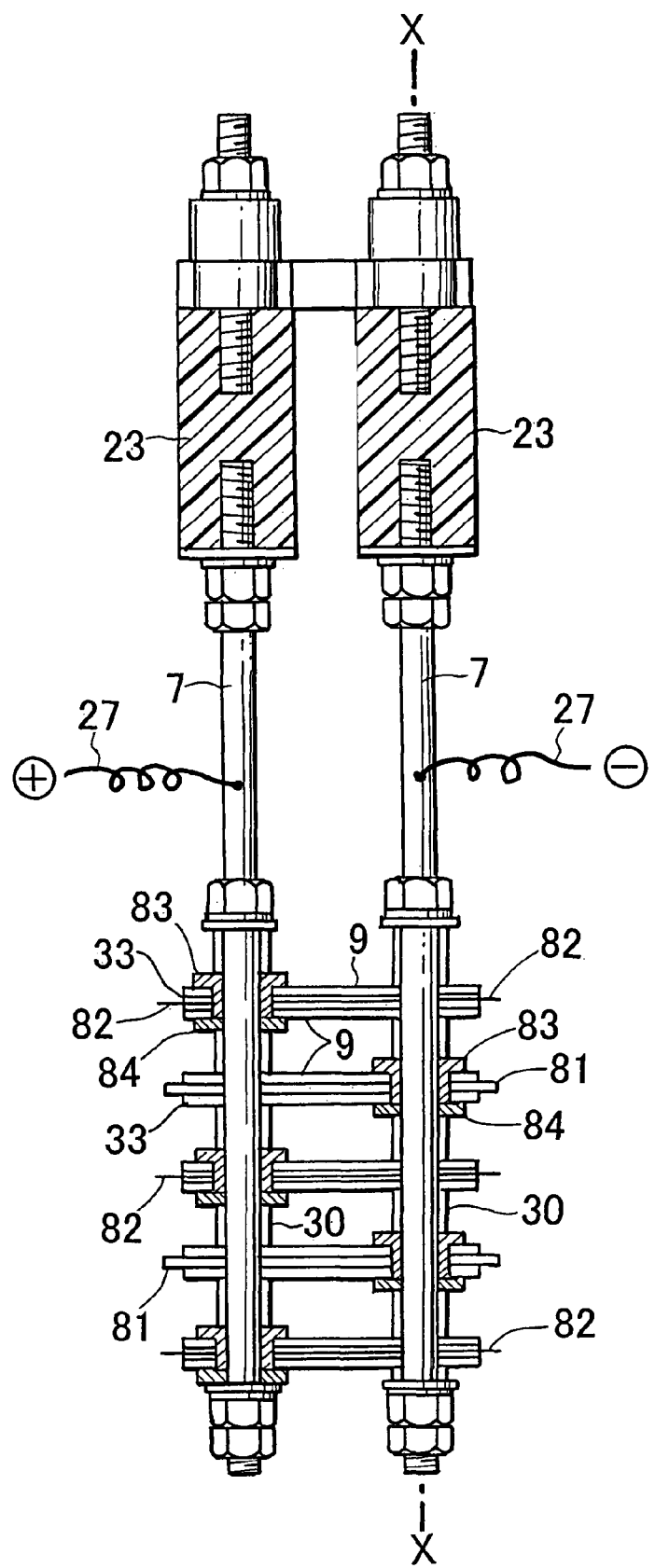
FIG. 14 is drawing showing an example of the vibrating blade placement in the third embodiment.
Figure 15:
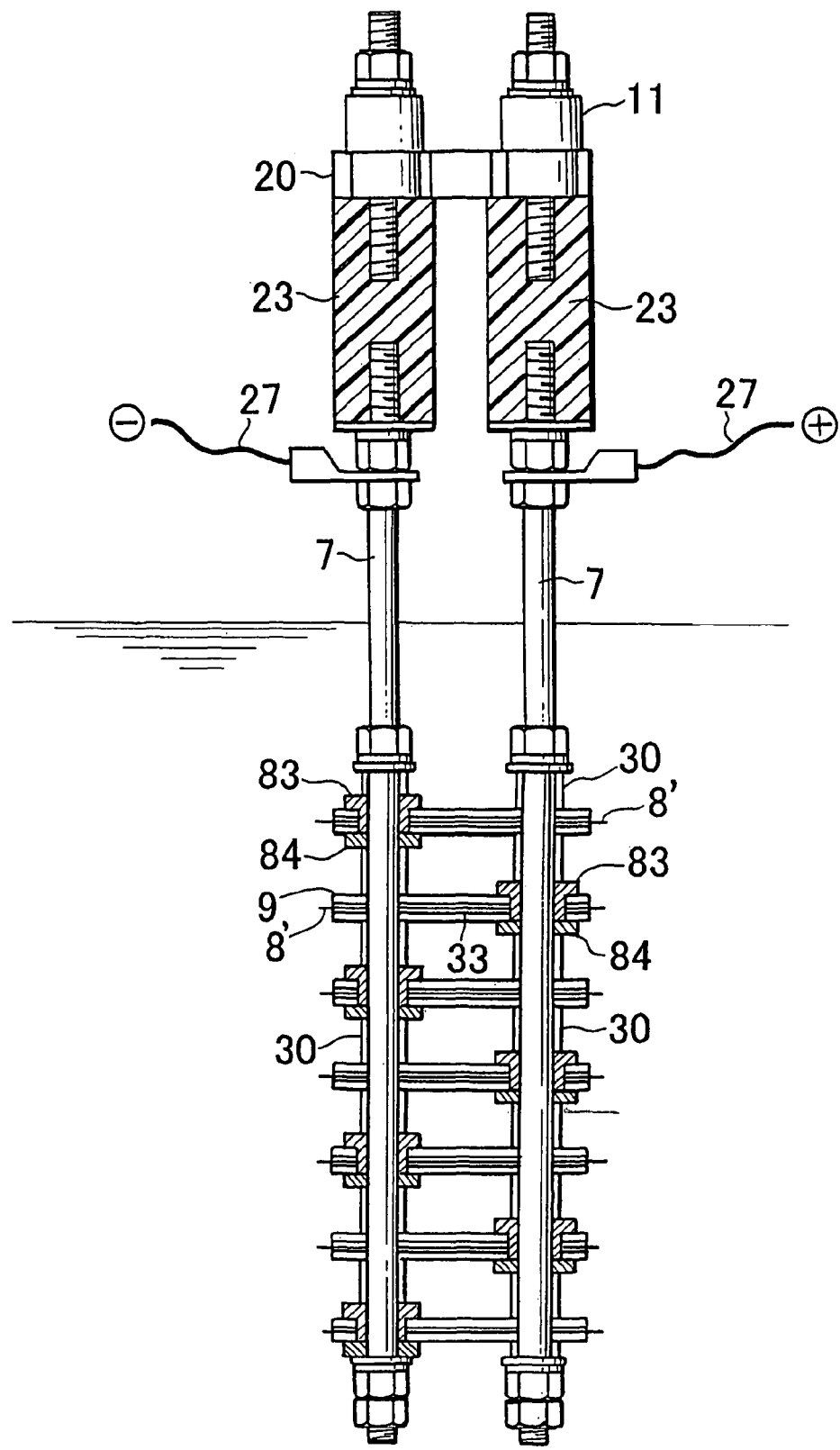
FIG. 15 is drawing showing an example of the vibrating blade placement in the third embodiment.
Figure 16:
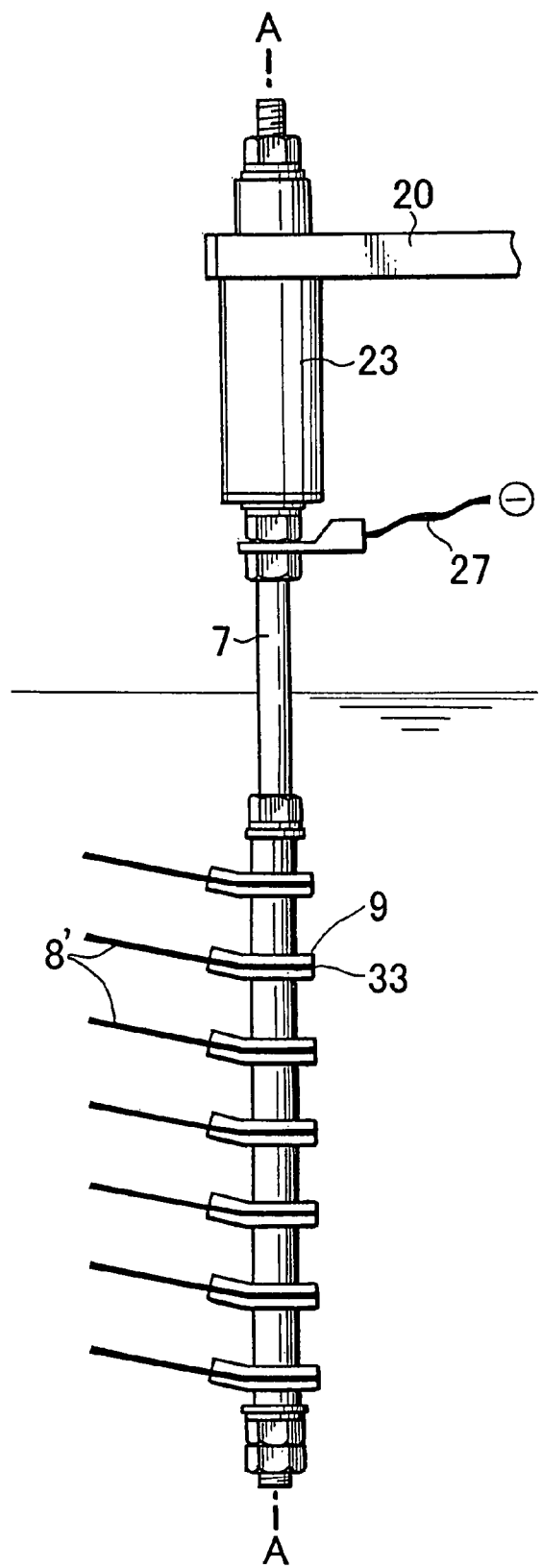
FIG. 16 is drawing showing an example of the vibrating blade placement in the third embodiment, and is a side view of FIG. 15.

FIG. 12 is a frontal view of this test device. The insulated type vibration-stirring means was utilized. The vibrating blades can be positioned by four methods in this device as shown in FIG. 13 through FIG. 16. The electrode plates and the vibrating blades are integrated together so that the overall device is compact. The number of vibrating blades is shown in the drawings.

The vibration motor supports were sealed in rubber per laid open patent JP-A No. 317295/2000.

The following reference numerals apply to FIG. 12 through FIG. 16.

20: first vibrating transmission member
23: cylindrical insulation member

Figure 17:
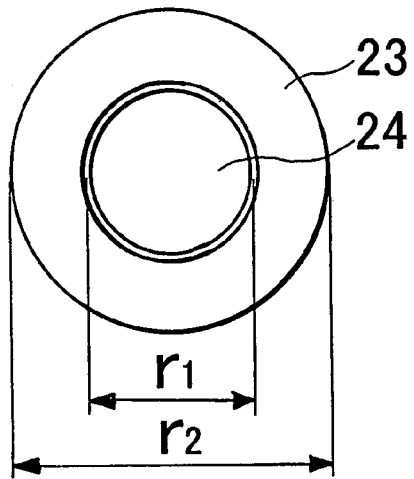
FIG. 17 is a drawing showing a top view of the cylindrical insulation member.
Figure 18:
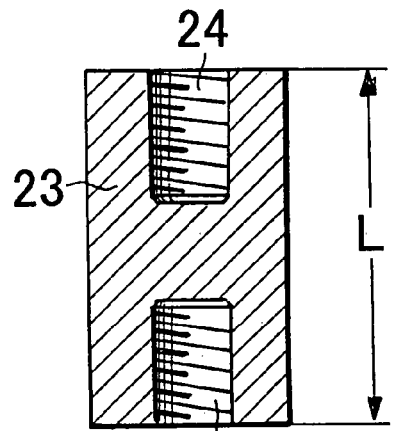
FIG. 18 is a drawing showing a cross-sectional view of the cylindrical insulation member.
Figure 19:
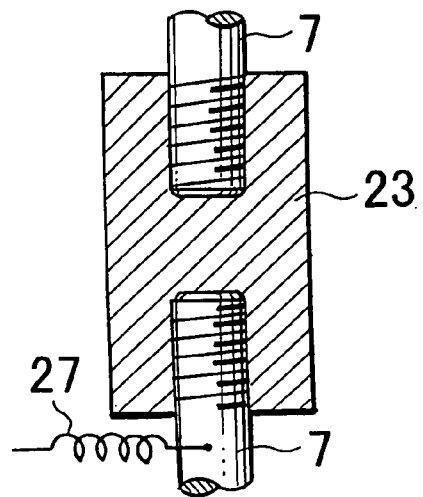
FIG. 19 is a drawing showing the state where the vibrating rods 7, 7 are fitting into the matching holes 24, in the cylindrical insulation member.

The cylindrical insulation member is further described next. The cylindrical insulation member 23 is equivalent to the first working model of the electrical insulation region. The cylindrical insulation member 23 is shown in detail in FIG. 17 through FIG. 19. FIG. 17 is top view of cylindrical insulation member 23, and FIG. 18 is a cross sectional view. The reference numeral 23 indicates the cylindrical (made of hard rubber) insulation member forming the insulation region. Holes or in other words, mating holes 24, 25 are formed at the top and bottom of the cylinder for mating the vibrating rods 7, or the vibrating rod with the vibration generating means. FIG. 19 shows the state where the vibrating rods 7,7 are fitted in the mating holes 24, 25. The reference numeral 27 denotes the electrical wire that makes the vibrating rods 7 and the vibrating blade 8 function as electrodes. In some cases, the electrode auxiliary blades can be used along with the vibrating blades 8. In this case, the vibrating blade need not always function as the electrode and may serve solely for vibration-stirring. The material for the vibrating blades at this time may be synthetic resin. The auxiliary blade 8 functions solely as an electrode, and may indicate almost no vibration stirring capability.

All other conditions, namely the (2) water for processing, (3) vibration flow, (4) bacteria types, and the (5) measurement methods were the same as the first embodiment.

(6) Physical Data on the Neutral Electrolytic Water
Hypochlorous acid content: 2 ppm
Residual chlorine content: 15 ppm
(Applications to Horticulture)

Unlike the first embodiment and the second embodiment, the vibrating blades are alternately made up of electrode plates. The electrode plates therefore do no have to be installed separately from the vibration-stirring device so the entire device can be made compact. Of the five vibrating blades on the 75 watt vibration-stirring device, three blades are anodes (positive electrodes) and 2 blades are cathodes (negative electrodes), and the tank capacity is approximately ½ the tank volume of the first embodiment. The vibration motor supports are sealed with rubber.

Salt of just 0.5 percent by weight was added to tap water the same as the first embodiment. Three anode blades and two cathode blades were installed on one 3-phase, 75 watt vibration motor and that motor then made to vibrate at 40 Hertz.

Three volts was applied for a 10 minute period and the neutral electrolytic water produced. This neutral electrolytic water was filled into coloration bottles and stored in a cool, dark location for a one month period. This neutral electrolytic water was used as water for cropped plants. The plants with this neutral electrolytic water lasted three time longer than those plants using only tap water.

The plants with neutral electrolytic water utilized as water for cropped plants were observed after a one week period. Those results are shown below.

After the snapdragon flower grown in neutral electrolytic water had wilted, its seeds sprouted the same as plants grown in soil.

Watercress grown in neutral electrolytic water possessed thick trunks, grew well, produced leaves and had a deep green color. All of them produced roots.

The watercress grown only in tap water all had narrow stems that narrowed finely. Watercress grown in the neutral electrolytic water developed the same as plants grown by hydroponic farming.

Fourth Embodiment (Applications for Cosmetics)
The neutral electrolytic water was produced for a 10 minute period according to the method of the second embodiment.
Physical data on the neutral electrolytic water
Hypochlorous acid content: 2 ppm
Residual chlorine content: 15 ppm
Activized element types: OH, $D_2$, HD and HDO On comparing the neutral electrolytic water of this invention with the strongly acidic electrolytic water obtained by three-chamber electrolyzing in terms of germicidal (sterilizing) power, when the neutral electrolytic water of this invention was used for hand washing disinfection, the germicidal effect continued for three days. The effect from the strongly acidic electrolytic water however was lost in one day. Moreover, roughened skin was prone to occur when using the strongly acidic electrolytic water. However there was little skin roughening when using the neutral electrolytic water of this invention.

The neutral electrolytic water of this invention was used as an oral disinfectant in dental surgery. Compared with the normally used water, corrosion of metal sections and waste water section of the equipment used in disinfecting was improved when the neutral electrolytic water of this invention was used. In particular, the finish rinsing required after using the acidic electrolytic water was no longer needed when the neutral electrolytic water of this invention was used. The neutral electrolytic water of this invention renders the same cleaning effects as the conventional alkali electrolytic water and possesses the same washing effects such as maintaining luster such as on hands, skin, and hair. Strongly acidic electrolytic water is known as not suitable for these applications.

This electrolytic water is used for the purposes of treating nasal inflammation, for mouthwash, and for oral hygiene. This electrolytic water has been found to be ideal for hand, skin and hair care.

The specified performance was still maintained for a one month period after breaking the seal. Use of strongly acidic water is required by law immediately after its production as recorded in the handling criteria and it is not sold in bottles.

After sealing and storing in a cool, dark location, the specified performance was still maintained after a one year period. The neutral electrolytic water of this invention was capable of emergency use and this was not achieved with electrolytic water of the related art.

Fifth Embodiment (Treatment of Burns)
Fried foods were being prepared for supper. Flying oil splashes caused a burn of approximately 3 by 7 millimeters on the fingertip. The pain felt from the burn promptly disappeared after spraying with the neutral electrolytic water (first embodiment) of this invention. Several minutes later, pain was again felt so this neutral electrolytic water was again sprayed. The pain once again vanished. When this was repeated another 1 to 2 times, the pain did not reoccur. After 3 or 4 days the skin no longer appeared red.

(Treating Injuries)
When the neutral electrolytic water (first embodiment) of this invention was sprayed on a knee injured in a fall, the wound healed extremely quickly.

(Cold Prevention)
After suffering from coughing or a runny nose, and the neutral electrolytic water of this invention (second embodiment) was then gargled or sprayed into the nasal cavity. The coughing ended during the night and the subject slept soundly until the following morning, and a stuff nosed was cured before becoming serious.

Figure 20:
FIG. 20 is a photograph of the buttocks prior to coating with the neutral electrolytic water.
Figure 21:
FIG. 21 is a photograph of the rear section after coating with the neutral electrolytic water.

(Preventing Skin Rash)
When the neutral electrolytic water (second embodiment) of this invention was coated on the buttocks of an elderly individual with repeating diaper rash, the skin peeling disappeared after one month. FIG. 20 and FIG. 21 show photographs of the buttocks before and after coating with the neutral electrolytic water of this invention. Though acidic electrolytic water possesses a germicidal effect it is not currently used in (medical) treatment.

(Treatment Test for Burns—2)
Ordinary acidic electrolytic water containing free chlorine at 20 ppm and the neutral electrolytic water (third embodiment) of this invention was utilized.

The ordinary acidic electrolytic water was sprayed on the burn several times a day but the burn was still not healed or soothed after five days had elapsed.

When the neutral electrolytic water of this invention was sprayed on the burn under the same conditions, the pain disappeared at a point 30 minutes after the spraying, and after five days the burn was completely healed.

Sixth Embodiment (Germicidal Test)

The neutral electrolytic water produced according to the third embodiment was filled as an undiluted solution into a handling spray type applicator. A triple dilute solution made up of this neutral electrolytic water diluted by three times, by adding tap water filled into the same type of applicator.

Test Method

1. Bacteria: Colon *bacillus* (*Escherichia coli* IFO3972)
2. Adjustment of the Test Bacteria Fluid The bacteria was transplanted to an ordinary Agar medium, and after culturing for 24 hours at 35° C., one colony was moved to an ordinary bouillon culture and vibrated for 18 hours for culturing at 35° C. This bacterial fluid was diluted and adjusted using ordinary bouillon.

3. Test Operation

Fifty milliliters of the test product was filled into a sterilized triangular flask of 100 milliliters capacity, and 0.1 milliliters of the test bacterial fluid adjusted above in 2 was also inserted and the flask then stored at 35° C.

4. Measuring the Number of Bacteria

The number of living bacteria per one milliliter in the triangular flask was measured at each elapsed time by the mixed dilute culture method utilizing an SCDLP Agar medium. An SCDLP bouillon culture was utilized for diluting during the measurement of the number of living bacteria.

Test Results

There was no change in the initial germicidal power even after a six month storage period. The germicidal power of the strongly acidic electrolytic water was lost from six months and onward.

TABLE 5

Germicidal test results for *staphylococcus aureus*

| Test water | Immediately after breaking the seal | After 30-seconds | After 1-Minute | After 3-Minutes | After 5-Minutes |
|---|---|---|---|---|---|
| Undiluted solution | $5.4 \times 10^6$ | Not-detected | Not-detected | Not-detected | Not-detected |
| After triple dilution | $5.4 \times 10^6$ | $1.7 \times 10^4$ | $5.6 \times 10^3$ | Not-detected | Not-detected |

Seventh Embodiment (Survival of Killifish)

Two 10 liter water tank units were prepared. Ordinary strongly acidic electrolytic water containing 10 ppm of free chlorine was inserted in one tank where 10 killifish were released. The neutral electrolytic water (second embodiment) of this invention was filled into the second tank where 10 killifish were also released. Killifish cannot be raised in tap water.

All killifish died 10 seconds after being released into the ordinary electrolytic water. On the other hand, three killifish survived for 5 days and the remaining seven killifish survived for seven days in the neutral electrolytic water of this invention.

Eighth Embodiment (Free Chlorine and Odors in Pools and Baths)

In pools and baths with free chlorine there was much damage from chlorine and odors even at free chlorine levels of 1 ppm. On the other hand, there was absolutely no chlorine damage or chlorine odor in the neutral electrolytic water (second embodiment) of this invention even at a free chlorine concentration of 10 ppm, to the contrary, the skin felt smooth after leaving the water. Ozone sterilizer is used as a pool disinfectant because chlorine is harmful to the eyes. The neutral electrolytic water of this invention was used however without ozone sterilizer (disinfectant) or UV irradiation. In hot springs (public baths) where strong alkaline electrolytic water is not used, the neutral electrolytic water of this invention retained its germicidal effect even in alkali hot springs (public baths).

Nineth Embodiment (Anti-Corrosion Test)

(1) Hydroelectrolysis Device

Utilized a neutral electrolytic water production device Model 1 (30 liters): a-Torino water production device Model 1 (made by Japan Techno Co., Ltd.)

(a) Vibration-Stirring Device

Vibration motor: 75 watts 200 volts×3-phase 1 unit

Vibrating blades: SUS304 4 plates

Vibration shaft: SUS304 2 rods (b) Electrolyte Tank

A container covered with heat-resistant propylene resin: 500×290×305 (unit: mm) was utilized.

(c) Electrodes

Anode plates: titanium plates covered with platinum 3 plates

Cathode plates: titanium plates 4-plates

Electrode gap: 30 mm

The anode plates and cathode plates are alternately installed.

The surface area of the electrode plates was 4.8 dm² for the four cathode plates; and 6 dm² for the three anode plates.

(d) Rectifier

Chuo Seisakusho (Corp.) PEM11-12V-200

(e) Inverter

Made by Fuji Electric (Inc.) Fuji Inverter FVR-C9S (2) Water: Soft Water=1:19 (Well Water, and Good for Drinking Water)

Salt (reagent class) was added, to adjust the electrolytic water to at 0.3 percent (3 grams per liter) by weight.

Three volts of direct current was applied and electrolyzing performed. The frequency of the vibrating blades was set to 40 Hertz and the electrolyzing time was set to 60 minutes. The residual chlorine content reached 300 ppm. The pH was 6.8. Power was applied and no rise in temperature in the electrolytic water was observed.

Hypochlorous acid content: 20 ppm

Activized element types: OH, $D_2$, HD and HDO

The above described electrolytic water was next filled into transparent bottles (one liter) and stored in a cool, dark location for a one month period. It was then diluted 10 times and used for the test.

Chinese cabbage was immersed in this neutral electrolytic water and then the Chinese cabbage was promptly removed and left standing for two weeks. The Chinese cabbage maintained its original state with no withering. On the other hand, when unprocessed water was used, then withering occurred and the cabbage lost its freshness.

When just picked fruit (apples, pears, etc.) were immersed in the neutral electrolytic water of this invention, that fruit maintained its freshness compared to unwashed fruit, and no internal discoloration was observed.

Tenth Embodiment

Figure 22:
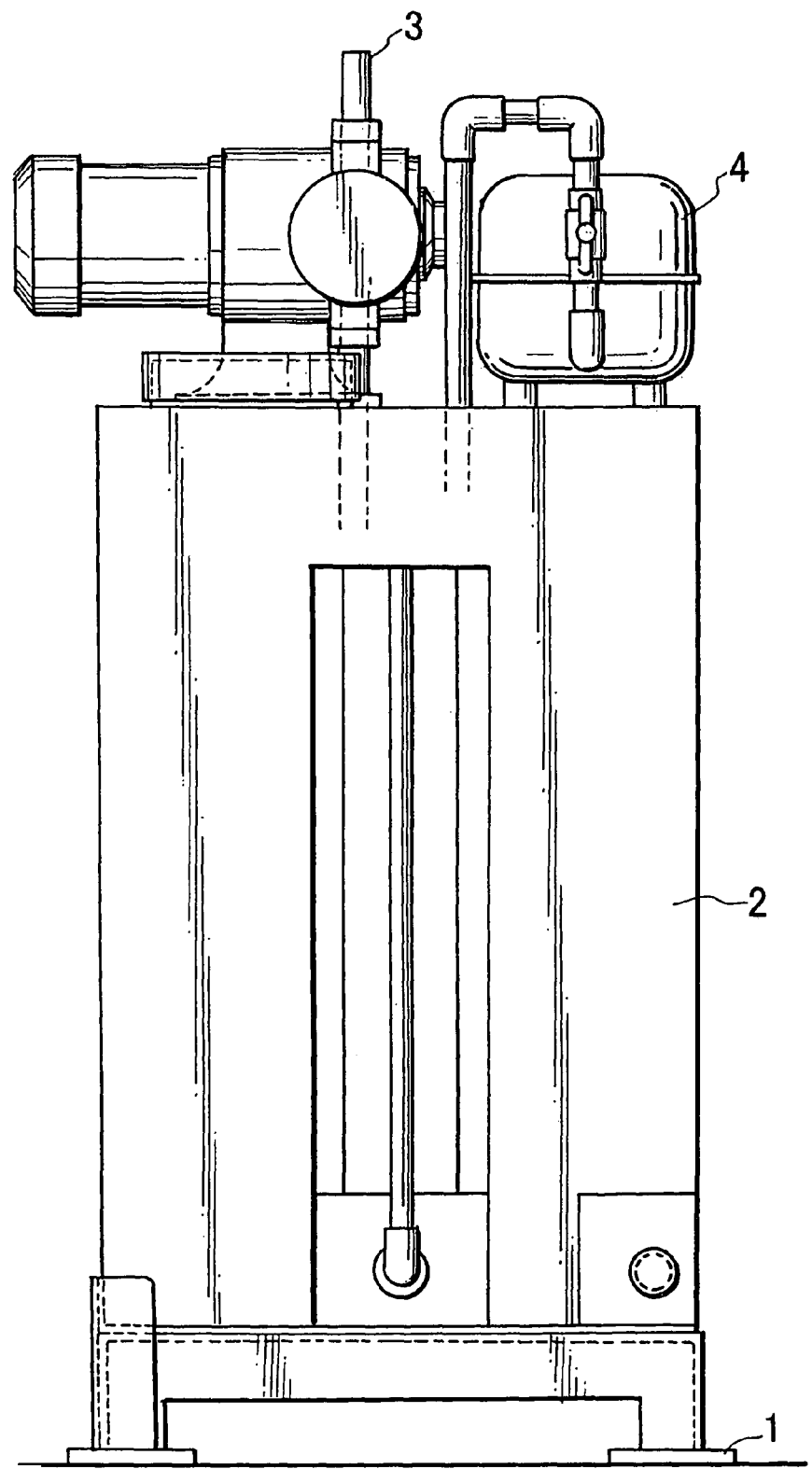
FIG. 22 is a frontal view of the auxiliary electrolyte tank in the tenth embodiment.
Figure 23:
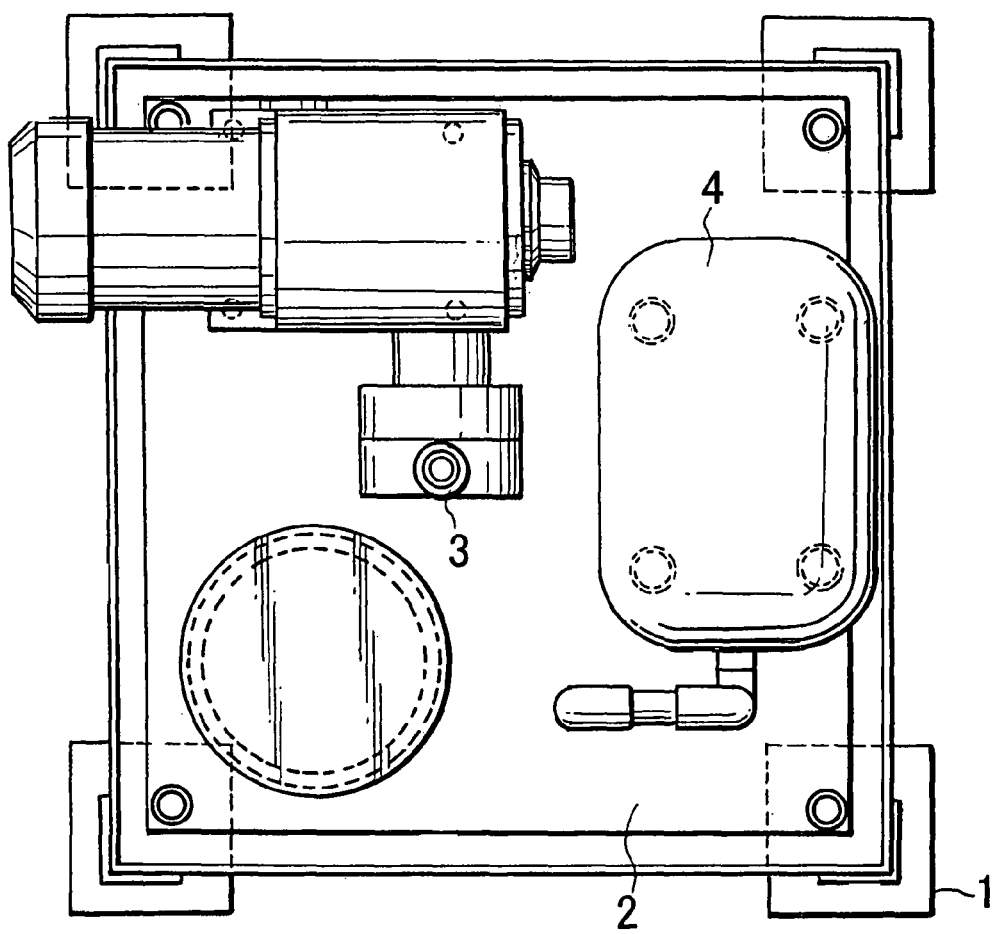
FIG. 23 is a plan (flat) view of the auxiliary electrolyte tank in the tenth embodiment.
Figure 24:
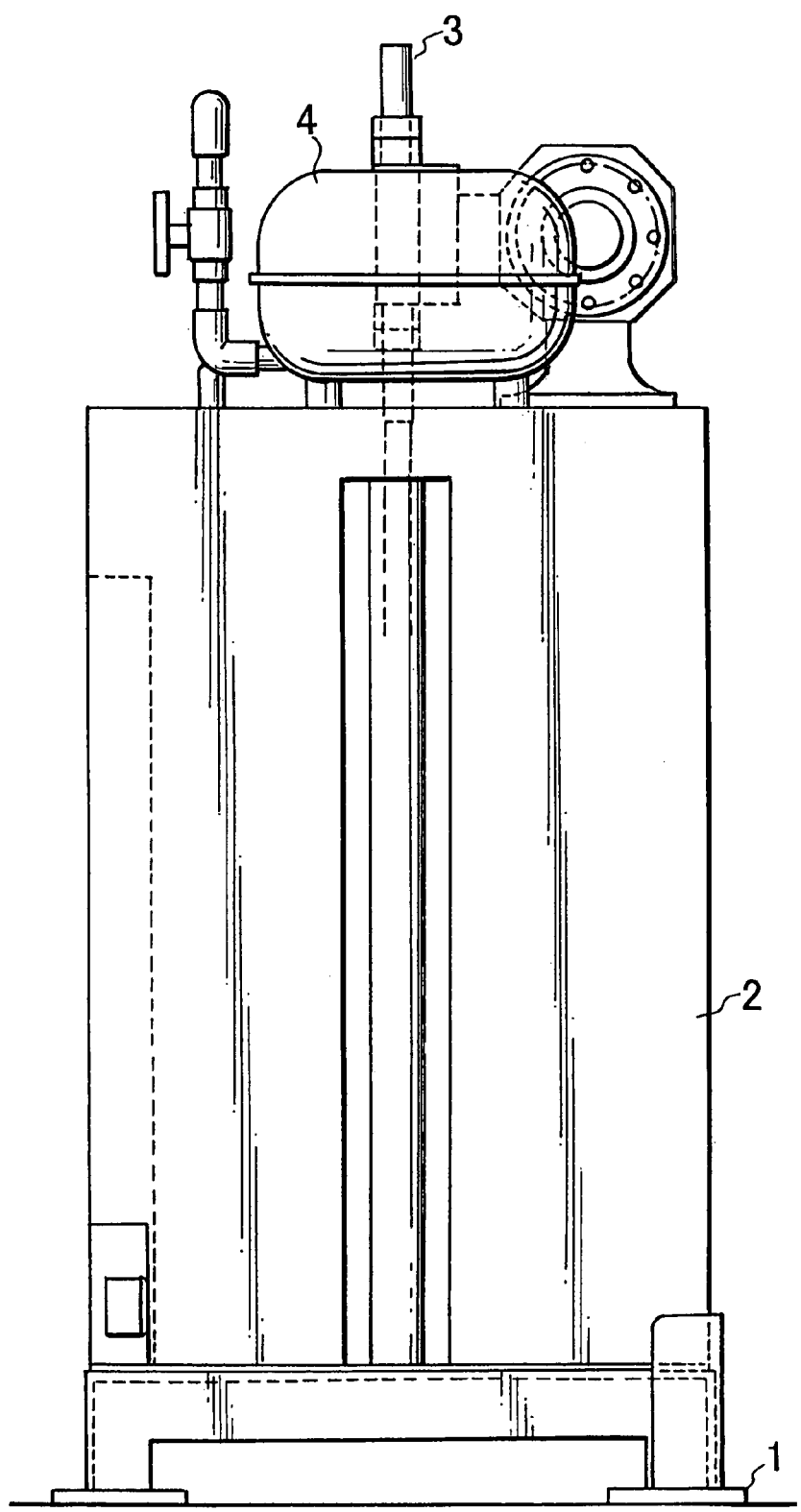
FIG. 24 is a side view of the auxiliary electrolyte tank in the tenth embodiment.
Figure 25:
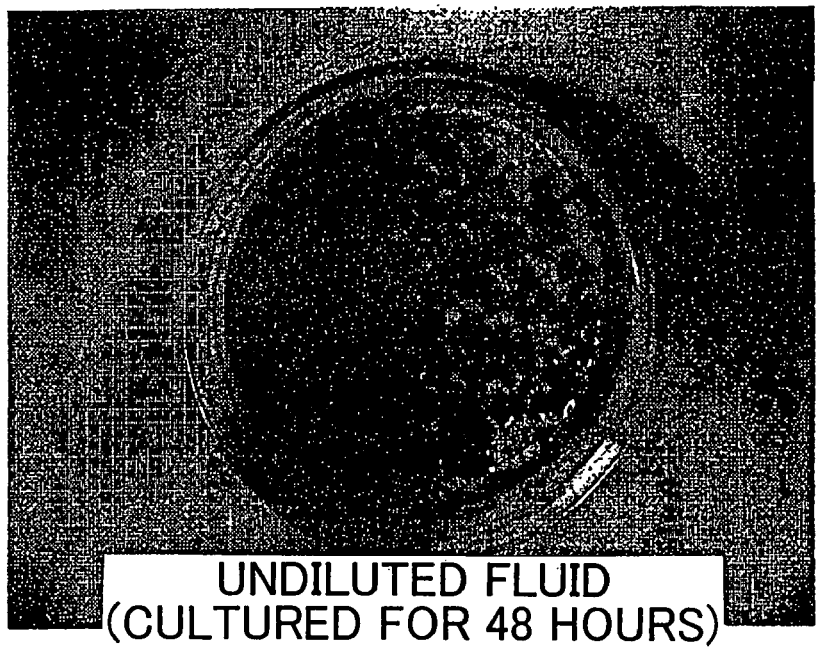
FIG. 25 shows the effect of neutral electrolytic water of the present invention in preventing growth of colon *bacillus* or *Escherichia coli*.
Figure 26:
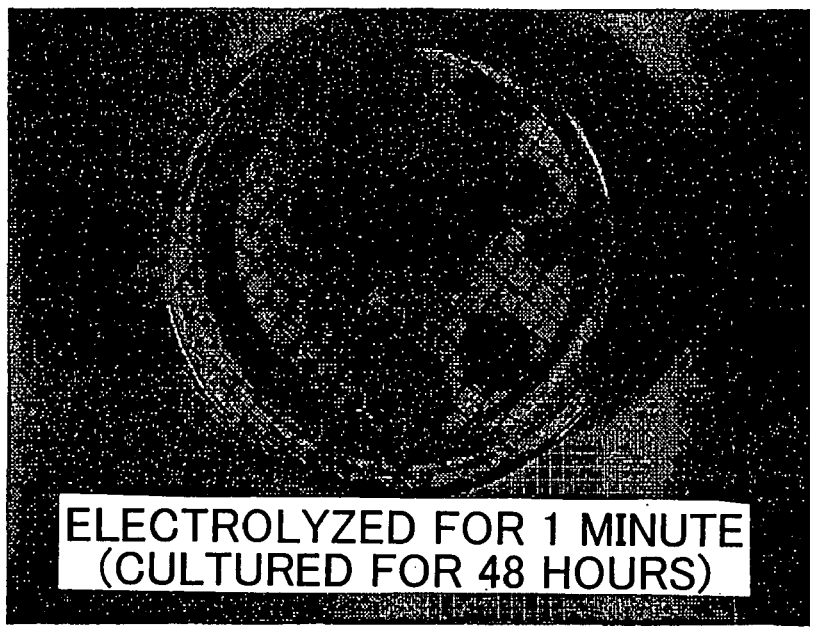
FIG. 26 shows the effect of the neutral electrolytic water of the present invention in preventing growth of colon *bacillus* or *Escherichia coli* obtained after performing electrolysis for one minute.
Figure 27:
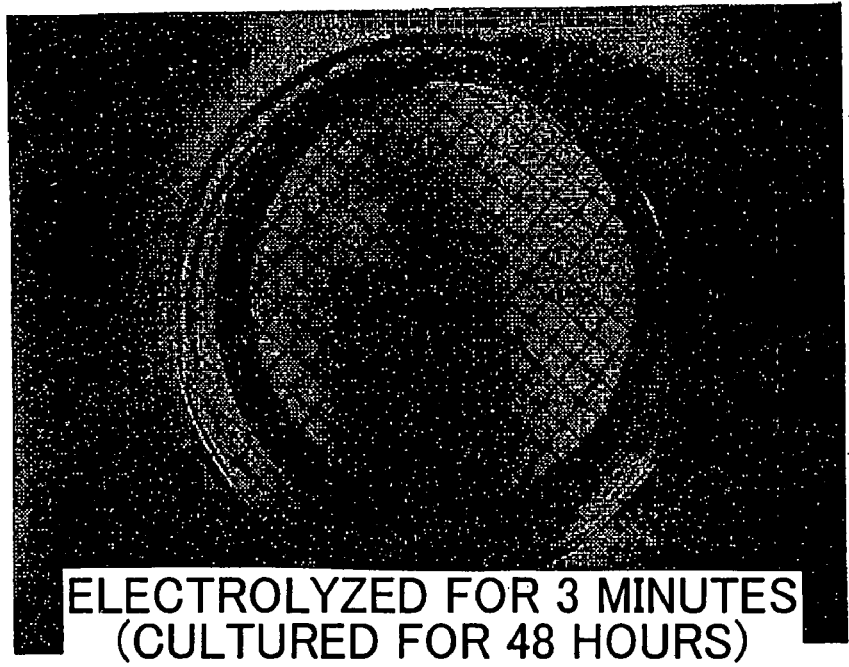
FIG. 27 shows the effect of the neutral electrolytic water of the present invention in preventing growth of colon *bacillus* or *Escherichia coli* obtained after performing electrolysis for three minutes.
Figure 28:
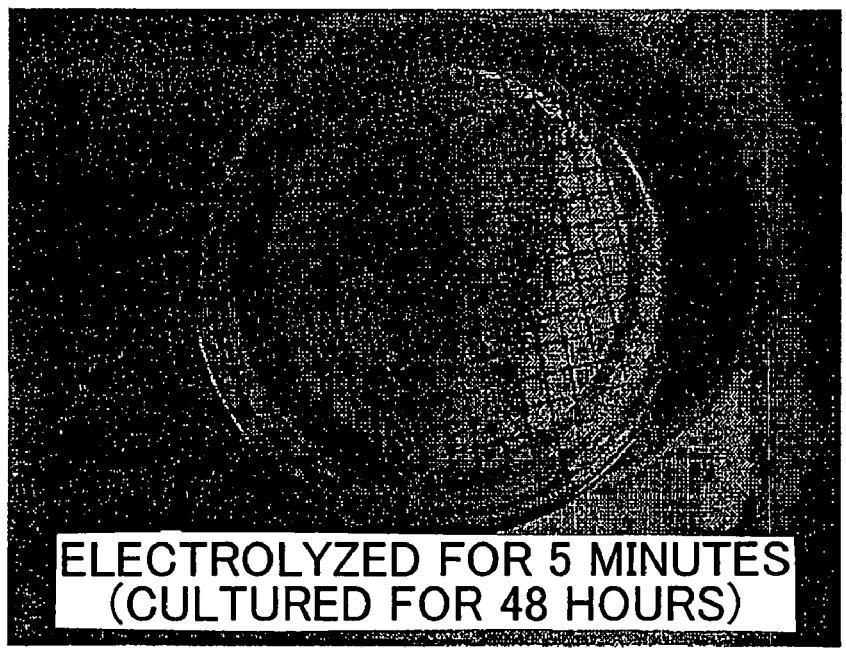
FIG. 28 shows the effect of the neutral electrolytic water of the present invention in preventing growth of colon *bacillus* or *Escherichia coli* obtained after performing electrolysis for five minutes.

The auxiliary electrolyte tank shown in FIG. 22 though FIG. 24 (capacity: 100 liters) was installed onto the device of the ninth embodiment.

Reference numerals for the auxiliary electrolyte tank

| | |
|---|---|
| 1 | frame |
| 2 | tank |
| 3 | pump dispensing outlet |
| 4 | stirring blower |

This auxiliary tank was joined to the electrolyte tank by a pipe. Neutral electrolytic water was continuously produced according to the ninth embodiment using tap water. Approximately 4.5 liters per minute were produced. Processing was able to continue for a long time. This test was performed continuously over a one year period but no drop in performance was found.

Hypochlorous acid content: 2 ppm
Residual chlorine content: 20 ppm
Activized element types: OH, $D_2$, HD and HDO Eleventh Embodiment (Neutral Electrolytic Water Applications)

The neutral electrolytic water produced in the method of the ninth embodiment was used as cosmetic material or external skin solution. There were almost no inferior points in terms of usage sensation or maintaining luster compared to commercially sold astringent lotion.

The above neutral electrolytic water was apportioned into external use pharmaceutical products such as soft ointments, dispersers, cream solutions and cosmetic material such as milky lotion, skin lotion (or facial lotion), packs, shampoos, and rinses; and the viscosity was adjusted with soluble macromolecular compounds such as stiffeners, emulsifiers, skin membrane formers. Ordinary strongly acidic electrolytic water cannot be used for these applications.

Twelfth Embodiment

The interrelation between the elapsed time after starting device operation and the residual chlorine content was investigated.

(1) Hydroelectrolysis Device

Neutral electrolytic water was produced by utilizing the same device as in the second embodiment.

Storage tank capacity: 100 liters (2) Electrolytic Water

Salt was liquefied in tap water and the concentration adjusted to 0.4 percent (4 grams per liter) by weight.

(3) Vibration Flow

The vibrating frequency of the vibration motor was adjusted to 43.8 Hertz.

TABLE 6

| Residual chlorine content | | | |
|---|---|---|---|
| Elapsed time (min.) | Electrical current (A) | Voltage (V) | Residual chlorine content (ppm) |
| 0 | 80 | 11.1 | 2 |
| 5 | 80 | 11.1 | 10 |
| 10 | 80 | 11.1 | 35 |
| 15 | 80 | 11.1 | 60 |
| 20 | 80 | 11.1 | 80 |
| 25 | 80 | 11.1 | 90 |
| 50 | 80 | 11.1 | 180 |

Thirteenth Embodiment

The interrelation between the elapsed time after starting device operation and the residual chlorine content was investigated.

(1) Hydroelectrolysis Device

Neutral electrolytic water was produced by utilizing the same device as in the second embodiment.

Storage tank capacity: 100 liters (2) Electrolytic Water

Salt was liquefied in tap water and the concentration adjusted to 0.3 percent (3 grams per liter) by weight.

(3) Vibration Flow

The vibrating frequency of the vibration motor was adjusted to 43.8 Hertz.

TABLE 7

| Residual chlorine content | | | |
|---|---|---|---|
| Elapsed time (min.) | Electrical current (A) | Voltage (V) | Residual chlorine content (ppm) |
| 0 | 70 | 12.9 | Not-detected |
| 5 | 70 | 13.0 | 10 |
| 10 | 70 | 12.9 | 20 |
| 15 | 70 | 12.8 | 30 |
| 20 | 70 | 12.7 | 40 |
| 30 | 70 | 12.6 | 50 |
| 60 | 70 | 12.7 | 100 |
| 60 | 350 | 12.6 | 500 |

Fourteenth Embodiment

The neutral electrolytic water produced according to the method of the first embodiment was next filled in bottles and stored for a three month period and its germicidal effect was then tested. Ordinary strongly acidic electrolytic water maintained its initial germicidal effect. However after 3 months that germicidal effect was mostly lost.

1. Bacteria Types

Colon *bacillus* (clinical drug resistant bacteria cultures)
*Staphylococcus aureus* (MRSA culture)
*Salmonella bacillus* (SE culture)
*Pseudomonas aeruginosa* (clinical drug resistant bacteria cultures)
*Legionella* (culture detected in baths)

2. Two milliliters of neutral electrolytic water was added to 200 microliters of fluid for each of the above six types of bacteria. After mixing, the mixture was let to sit. 100 microliters of bacterial fluid was then incubated after 30 seconds, 60 seconds, 90 seconds, 120 seconds, 3 minutes, 5 minutes, 10 minutes, and 20 minutes.

3. Bacteria concentration (content)

All were pure cultivated so the bacteria fluids were 105 through 106.

4. Test results

Results were rated as follows:
+: if growth was found
−: if growth was not found Results are shown in Table 8 and Table 9.

TABLE 8

Bacterial fluid 200 microliters + 2 milliliters of neutral electrolytic water (immediately after production)

| Bacteria type | 30 seconds | 60 seconds | 90 seconds | 120 seconds | 3 minutes | 5 minutes | 10 minutes | 20 minutes |
|---|---|---|---|---|---|---|---|---|
| Colon bacillus | − | − | − | − | − | − | − | − |
| Staphylococcus aureus | + | + | − | − | − | − | − | − |
| Salmonella | + | + | + | − | − | − | − | − |
| Pseudomonas aeruginosa | − | − | − | − | − | − | − | − |
| Legionella | + | − | − | − | − | − | − | − |

TABLE 9

Bacterial fluid 200 microliters + 2 milliliters of neutral electrolytic water (3 months after production)

| Bacteria type | 30 seconds | 60 seconds | 90 seconds | 120 seconds | 3 minutes | 5 minutes | 10 minutes | 20 minutes |
|---|---|---|---|---|---|---|---|---|
| Colon bacillus | − | − | − | − | − | − | − | − |
| Staphylococcus aureus | + | + | − | − | − | − | − | − |
| Salmonella | + | + | + | − | − | − | − | − |
| Pseudomonas aeruginosa | − | − | − | − | − | − | − | − |
| Legionella | + | − | − | − | − | − | − | − |

Fifteenth Embodiment

The same vibration-stirring device as in the third embodiment was utilized.

The electrode plates within the tank were the same as those in FIG. 6 and FIG. 7.

Electrolyte tank: heat-resistant propylene resin: capacity 200 liters

Vibration-stirring device: Vibratory Agitator type 2

Vibration motor 150 watts×200 volts×3-phase dual shaft type

Vibrating blades 5 blades titanium

Vibration shaft 2 shafts titanium

Electrode Plates in Electrolyte Tank

Anode platinum 3 plates

Cathode titanium 4 plates

Electrode gap 5 millimeters

Electrolytic Water (1) KCl 0.5% reagent 2-class product (2) $CaCl_2$ 0.5% reagent 2-class product The above electrolytic water was placed in the tank, the vibration-stirrer operated at room temperature, and it was completely liquefied in about five minutes.

Inverter Fujitsu FVR-E9S

Use 0.1 to 3.7 kilowatts with a 200 volt 3-phase input.

The vibration motor was rotated for 45 minute, and 5 volts of direct current applied to the electrolytic water for 15 minutes. The same task was performed in the case of NaCl.

The germicidal test was performed using O-157 bacteria.

Culturing was performed for 24 hours while complying with the JIS general bacterial method.

The strongly acidic electrolytic water from the 3-chamber device possessed only a slight germicidal effect the same as the above embodiments and so was not practical to use.

TABLE 10

| | Germicidal test | | | | | | |
|---|---|---|---|---|---|---|---|
| Salt | Residual chlorine | 0-Minutes | 2-Minutes | 5-Minutes | 10-Minutes | Chlorine odor | Hypochlorous acid |
| KCl | 20 ppm | $5.1 \times 10^7$ | Not-detected | Not-detected | Not-detected | None | 2 ppm |
| $CaCl_2$ | 22 ppm | $4.8 \times 10^7$ | Not-detected | Not-detected | Not-detected | None | 2 ppm |

Note:
Here, "Not detected" signifies less than 40 particles per nL.

There was no chlorine odor and the germicidal effect was the same as NaCl.

The neutral electrolytic water eliminated odors from pet dog excrement.

The neutral electrolytic water was found to be usable for cleaning laboratory floors. However it was not usable in the case of stubborn stains or dirt. The neutral electrolytic water was usable if used in combination with alkaline cleanser.

The effect was confirmed when the germicidal test was performed after placing in a bottle and storing for a three month period.

Sixteenth Embodiment

The neutral electrolytic water of the fifteenth embodiment was stored in a polyvinyl tank (16 liters) for a three month period and water quality tests of the undiluted fluid performed. The residual chlorine contents were at the water quality standard of 250 ppm or lower.

The effect was confirmed when this liquid was placed in a small, plastic spray container and used for oral disinfection and dental oral washing. In the case of acidic electrolytic water, rinsing with tap water is required after oral disinfection, however this finish-rinsing was not required when using the neutral electrolytic water of this invention. This neutral electrolytic water can also be used as mouthwash water (for gargling) or drinking water.

A dedicated humidity adjustor was used to adjust the humidity within a building. This humidity adjustment however was performed by installing a large spray device (for the neutral electrolytic water) in the customer reception room within the building and the results were well rated. This device currently is still continuously being used. Germs were increasing within the air conditioning water within a building and the effect on the cooling equipment and water flying outwards were a problem. These problems were resolved by using the neutral electrolytic water of this invention. Strongly acidic water is difficult to use for circulation and is not economical in terms of the water quantity.

The following items were confirmed in terms of actual performance of the neutral electrolytic water of this invention.

1) The neutral electrolytic water deodorized and cleaned the indoor air.

2) When fresh food products such as fruits or vegetables were sprayed with this neutral electrolytic water and then placed in a refrigerator, they were effectively disinfected, and could be stored for longer periods.

3) Spraying the neutral electrolytic water on the hands disinfected and sterilized them.

4) The neutral electrolytic water prevented mold from occurring.

5) The neutral electrolytic water disinfected and sterilized kitchen knives and cutting boards.

6) The neutral electrolytic water deodorized pets such as dogs, cats and birds.

Seventeenth Embodiment

Seawater was processed utilizing the neutral electrolytic water production device of this invention.

(1) Test Device: a-Torino Water Production Device Model 1

(a) Vibratory Agitator type 2 Vibration motor dual shaft type 75 watts×200 volts 3-phase vibrating-lades vibration-shaft stainless steel (SUS304)

Cathode electrode plate SUS304 4-plates anode electrode plate platinum film covering (3 plates)

(b) Electrolyte tank: heat-resistant propylene: capacity 30 liters (500×250×305 mm)

(c) Regulator Chuo Seisakusho PME11-12V-200

(d) Inverter Fuji Denki (Inc.) FVR-C11S model (2) Test Method

The vibration cycle of the vibration-stirring device was adjusted to 45 Hertz with the inverter. Electrolyzing of the sea water was performed by applying a fixed electrical current at a voltage of 10 to 11 volts, and electrical current of 20 amperes at a processing time of 5 minutes.

(3) Test Results

Neutral electrolytic water with a pH of 7.6 and a residual chlorine content of 700 ppm was obtained (hereafter called neutral electrolytic water (originally seawater). A germicidal test was performed by using the neutral electrolytic water as the sterilizing water. This neutral electrolytic water was placed in a fishing water tanks, a portion of it was frozen. When a test was then performed using the neutral electrolytic water for preserving fish (young yellowtail, sardines) caught from the open sea, the fish showed no damage at least from transporting from the fishing grounds to land, and were maintained in a satisfactory fresh state.

Eighteenth Embodiment

A germicidal test was performed under the following conditions.

<Test Method>

(Test preprocessing) The processing device was washed and sterilized with alcohol.

(Electrolyzing) Electrolyzing was performed at 3.57 volts and 5 amperes (fixed current) and sampling of the test piece performed at each of the following times.

(1) Prior to performing electrolyzing (seawater)

(2) Sampling after 1 minute of electrolyzing (1 minute processing of neutral electrolytic water)

(3) Sampling after 3 minutes of electrolyzing (3 minute processing of neutral electrolytic water)

(4) Sampling after 5 minutes of electrolyzing (5 minute processing of neutral electrolytic water) (Incubation processing) Colon *bacillus* was incubated for 48 hours (culture: ordinary sterilizing SCD agar medium) using 4 test pieces in an incubator (Yamato incubator: IC340S).

(Test Results)

Results are shown in FIG. 25 through FIG. 28. A colon *bacillus* colony was observed in sea water processing but the colony quantity decreased over a time from 1 to 5 minutes, and almost no colonies were observed in the 3 and 5 minute processed neutral electrolytic water.

These results show a satisfactory example for a method for preventing fish from rotting and maintaining freshness by using the neutral electrolytic water and the neutral electrolytic water production device of this invention.

A) To produce the neutral electrolytic water, the content of the water for processing is usually changed by adding 0.05 to 8 percent salt to the water such as tap water or ion exchange water to obtain salt water and then electrolyzing it. In this case, the electrolyzing is preferably performed at an electrical current density of 0.05 A/L-5A-L. The time for the electrolyzing is preferably 10 to 90 minutes.

In fields utilizing a means for preventing decay by freezing ordinary water, the neutral electrolytic water of this invention can also be utilized as a "germicidal ice" and demonstrated a powerful decay prevention effect. The preservation of the raw foods was improved, and its safety was enhanced.

(B) Seawater may also be utilized instead of the above described salt water. In that case, the seawater is filled into the electrolyte tank of the neutral electrolytic water production device of this invention preferably under electrolyzing conditions where the free chlorine content becomes 50 ppm to 2000 ppm. Neutral electrolytic water made under these conditions will penetrate into the internal organs of the caught fish. The caught fish are then covered with ice made of this electrolytic water. This method can completely sterilize and prevent partial decay, and the fish can be transported as is, in a fresh state to land.

The neutral electrolytic water production device of this invention can also be utilized while installed for example on a fishing boat. In this case, a "germicidal ice" possessing powerful germicidal characteristics and a decay prevention effect can be produced by the neutral electrolytic water production device of this invention using seawater, and used to maintain the freshness of the fish.

Moreover, the neutral electrolytic water of this invention possesses a strong decay prevention effect that is also highly safe since it does not generate hazardous substances such as sodium hypochlorite.

Nineteenth Embodiment

Figure 29:
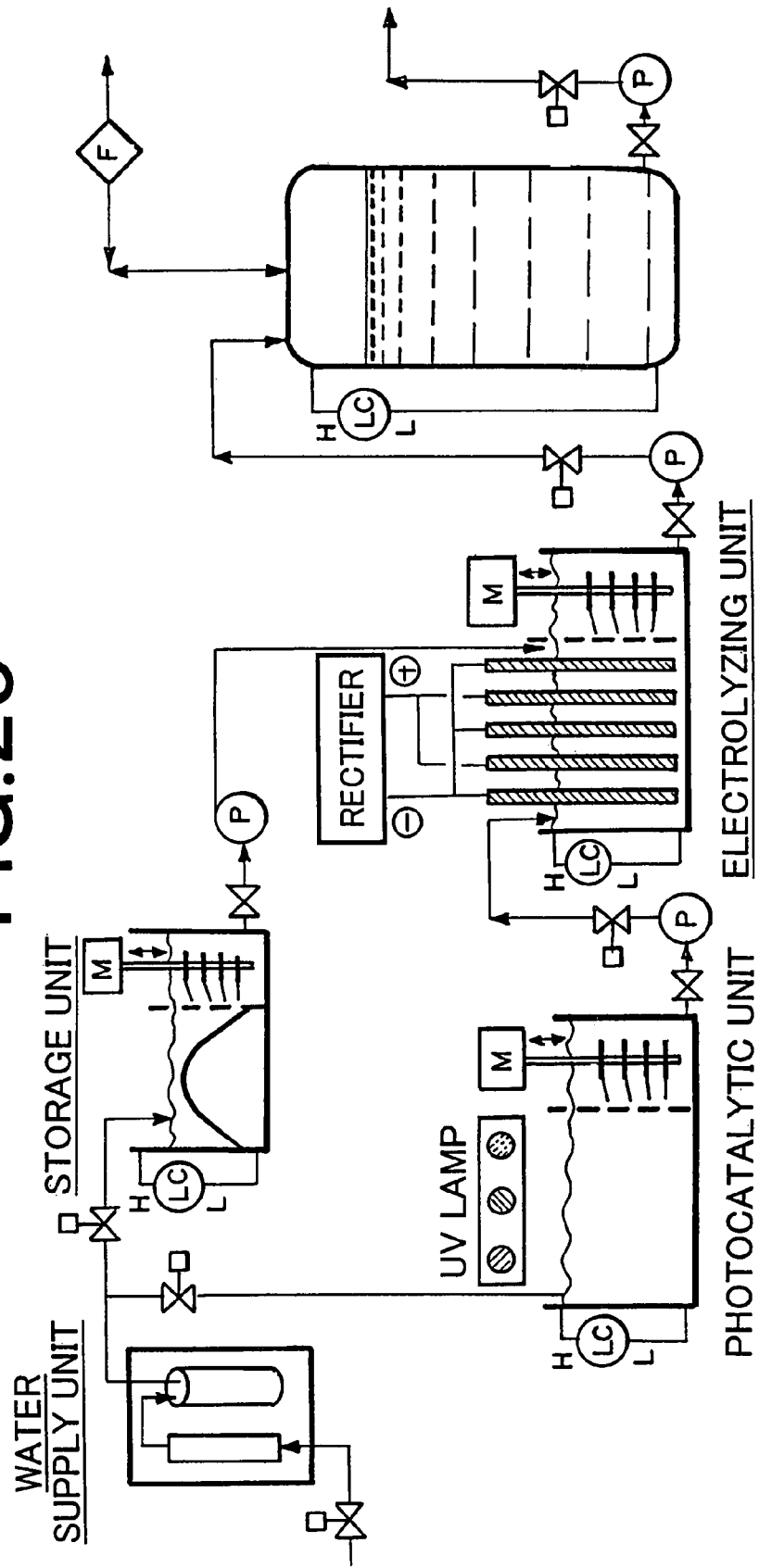
FIG. 29 is a drawing showing an overall view of the neutral electrolytic water production device of this invention including a photocatalytic processing unit.

The neutral electrolytic water obtained by electrolyzing at a fixed electrical current in conformance with the method for producing neutral electrolytic water of this invention by utilizing a device described in FIG. 29 including a photocatalytic unit containing a vibration-stirring device surface-treated utilizing anatase titanium oxide activized by ultraviolet rays, was evaluated as follows. Those results are shown in Table 11.

<Measurement Conditions>
Water for processing: 17.5 g NaCl/14.4 L water
Rectifier: DC12V-20A
Electrode gap: 20 millimeters (2 electrodes are platinum anodes, and 3 are titanium cathode electrodes)
Vibrating conditions: frequency 44 Hertz

TABLE 11

Neutral electrolytic water of this invention produced by photocatalytic processing of water

| Elapsed time (min.) | Electrical current (A) | Voltage (V) | Residual chlorine content (mg/L) | pH |
| --- | --- | --- | --- | --- |
| 0 | 7.1 | 12.11 | Not detected | — |
| 60 | 7.1 | 11.68 | 18 | — |
| 120 | 7.2 | 11.43 | 32 | — |
| 180 | 7.3 | 11.1 | 50 | — |
| 210 | 7.3 | 11.05 | 50 | 7.86 |

Industrial Applicability

The effect as described above that is rendered by the neutral electrolytic water of this invention lasts for a long period of time, and this neutral electrolytic water is likely to be utilized in a wide range of fields. Along with these uses, this neutral electrolytic water is also likely to be produced in ever greater amounts.

The invention claimed is:

1. A method for producing neutral electrolytic water containing OH, $D_2$, HD and HDO as active elements, including a process for electrolyzing a liquid for processing comprised of water and at least one type of salt selected from a group consisting of NaCl, KCl, and $CaCl_2$ by applying a direct current or pulsed current at a current density of 5 A/dm$^2$ to 300 A/dm$^2$ and a voltage from one to thirty volts, while vibrating a vibration motor of a vibration stirring device at a vibration frequency between 10 Hertz and 500 Hertz so as to vibrate a vibrating blade of the vibration stirring device immersed in the liquid at an amplitude from 0.01 to 30 millimeters
wherein the salt content of the liquid for processing is from 0.05 percent by weight to 10 percent by weight.

2. A method for producing neutral electrolytic water according to claim 1, wherein the electrolyzing process is performed from 5 to 90 minutes.

3. A method for producing neutral electrolytic water according to claim 1, wherein the liquid for processing is seawater.

4. A method for producing neutral electrolytic water according to claim 1, wherein the water includes tap water, underground water, well water, distilled water, soft water, ion replacement water and reverse osmosis membrane water.

5. A method for producing neutral electrolytic water according to claim 1, further including a photocatalysis process performed on the liquid for processing prior to the electrolyzing process.

6. A method for producing neutral electrolytic water according to claim 5, wherein the photocatalysis process is performed by making the liquid for processing come in contact with the photoactivated anatase titanium oxide.

* * * * *